(12) United States Patent
Ezura et al.

(10) Patent No.: US 10,385,357 B2
(45) Date of Patent: Aug. 20, 2019

(54) MUTANT PLANT

(71) Applicants: UNIVERSITY OF TSUKUBA, Ibaraki (JP); RIKEN, Saitama (JP)

(72) Inventors: Hiroshi Ezura, Ibaraki (JP); Tohru Ariizumi, Ibaraki (JP); Yoshihito Shinozaki, Ibaraki (JP); Junji Kimbara, San Jose, CA (US); Miyako Kusano, Saitama (JP); Atsushi Fukushima, Saitama (JP); Kazuki Saito, Saitama (JP)

(73) Assignees: UNIVERSITY OF TSUKUBA, Tsukuba-shi, Ibaraki (JP); RIKEN, Wako-shi, Saitama (JP)

( * ) Notice: Subject to any disclaimer, the term of this patent is extended or adjusted under 35 U.S.C. 154(b) by 328 days.

(21) Appl. No.: 15/034,455

(22) PCT Filed: Nov. 7, 2014

(86) PCT No.: PCT/JP2014/079552
§ 371 (c)(1),
(2) Date: May 4, 2016

(87) PCT Pub. No.: WO2015/068794
PCT Pub. Date: May 14, 2015

(65) Prior Publication Data
US 2016/0264989 A1 Sep. 15, 2016

(30) Foreign Application Priority Data
Nov. 7, 2013 (JP) ................ 2013-231495

(51) Int. Cl.
C12N 15/62 (2006.01)
C12N 15/82 (2006.01)
A23L 19/00 (2016.01)
A01H 5/10 (2018.01)

(52) U.S. Cl.
CPC ........... *C12N 15/8273* (2013.01); *A01H 5/10* (2013.01); *A23L 19/00* (2016.08); *C12N 15/8261* (2013.01); *C12N 15/8262* (2013.01); *A23V 2002/00* (2013.01); *Y02A 40/146* (2018.01)

(58) Field of Classification Search
None
See application file for complete search history.

(56) References Cited

FOREIGN PATENT DOCUMENTS

WO   WO 2011/054998   5/2011   ......... C12N 15/8218

OTHER PUBLICATIONS

Carrera et al ("Characterization of the procera Tomato Mutant Shows Novel Functions of the S1DELLA Protein in the Control of Flower Morphology, Cell Division and Expansion, and the Auxin-Signaling Pathway during Fruit-Set in Development", Plant physiology 160:1581-1596).*
Bowie et al, Science 247:1306-1310, 1990.*
McConnell et al, Nature 411 (6838):709-713, 2001.*
Carrera et al (2012, Plant physiology 160:1581-1596).*
Extended European Search Report from corresponding European Application No. 14859851.9, dated Apr. 6, 2017.
Marti et al., The Plant Journal, vol. 52, 2007, pp. 865-876.
Bevan, M. (Nov. 1984) "Binary *Agrobacterium* vectors for plant transformation." *Nucleic Acids Res.*, 12(22): 8711-8721.
Carrera, E., et al. (Nov. 2012) "Characterization of the *procera* tomato mutant shows novel functions of the S1Della protein in the control of flower morphology, cell division and expansion, and the auxin-signaling pathway during fruit-set and development[C][W]". *Plant Physiol.*, 160(3):1581-96, Epub Aug. 31, 2012.
Chandler, P.M., et al. (2013) "'Overgrowth' mutants in barley and wheat: new alleles and phenotypes of the 'Green Revolution' DELLA gene." *J.Exp.Bot.*, 64(6):1603-13, Epub Feb. 4, 2013.
Harberd, N.P., et al. (May 2009) "The angiosperm gibberellin-GID1-DELLA growth regulatory mechanism: how an "inhibitor of an inhibitor" enables flexible response to fluctuating environments." *Plant Cell*, 21(5):1328-39, Epub May 26, 2009.
Hirano, K., et al. (Aug. 2010) "Characterization of the molecular mechanism underlying gibberellin perception complex formation in rice." *Plant Cell*, 22(8):2680-96, Epub Aug. 17, 2010.
Ikeda, A., et al. (May 2001) "slender rice, a constitutive gibberellin response mutant, is caused by a null mutation of the SLR1 gene, an ortholog of the height-regulating gene GAI/RGA/RHT/D8." *Plant Cell*, 13(5):999-1010.
Lawit, S.J., et al. (2010) "Maize DELLA Proteins dwarf plant8 and dwarf plant9 as Modulators of Plant Development." *Plant Cell Physiol*, 51(11):1854-1868. Epub Oct. 11, 2010.
Ooms, G., et al. (1982) "Octopine Ti-plasmid deletion mutants of *Agrobacterium tumefaciens* with emphasis on the right side of the T-region." *Plasmid*, 7(1):15-29. Epub Nov. 1, 2004.
Weston, D.E., et al. (May 2008) "The Pea DELLA proteins LA and CRY are important regulators of gibberellin synthesis and root growth[W][OA]." *Plant PhysioL*, 147:199-205.
English Translation of International Search Report (ISR) dated Feb. 10, 2015 in International Patent Application No. PCT/JP2014/079552.
Notification of Transmittal of Translation of the International Preliminary Report Patentability (IPRP) (PCT/IB/338 & PCT/IB/373) for PCT/JP2014/079552, dated May 19, 2016.

* cited by examiner

*Primary Examiner* — Stuart F Baum
(74) *Attorney, Agent, or Firm* — Harness, Dickey & Pierce, P.L.C.

(57) ABSTRACT

Provided is a plant such as tomato, in which plant vigor has been increased and heat resistance has further been imparted. A plant such as tomato can be obtained, which has increased the stem diameter as well as the plant height and has become heat resistant by having a mutant Della protein, in which a leucine corresponding to the leucine at position 567 in SEQ ID NO: 2 in the amino acid sequence of the Della protein has been replaced by another amino acid, preferably phenylalanine.

8 Claims, 8 Drawing Sheets
Specification includes a Sequence Listing.

// MUTANT PLANT

CROSS-REFERENCE TO RELATED APPLICATIONS

This application is a national phase application of PCT Application No. PCT/JP2014/079552, filed on 7 Nov. 2014, which claims benefit of Japanese Patent Application 2013-231495, filed on 7 Nov. 2013. The entire disclosure of the applications identified in this paragraph are incorporated herein by references.

TECHNICAL FIELD

The present invention relates to a mutant plant that has an increase in plant vigor and exhibits an excellent heat resistance.

BACKGROUND

Tomato is eaten worldwide and also abundantly contains vitamins, minerals, lycopene and the like so that it is highly nutritious.

However, in terms of the area suitable for the cultivation thereof, sufficient growth is not always expected in any place and it is difficult in some areas to provide fresh fruits thereof. For example, for the cultivation thereof in an area where ambient temperature is high, the wilting of the plant body due to the heat has been a big problem in the growth of tomato plants.

Examples of an approach in plant breeding to solve this problem include breeding a tomato having an excellent heat resistance phenotype. An increased vigor in the plant body, that is, a combination of an increased plant height and an increased stem diameter is included as one of the important phenotypes thereof.

The height of a plant body is known to be increased in tomato by replacing valine at position 302 with glutamic acid in the amino acid sequence of the Della protein having a function to prevent the growth of a plant (Non-Patent Document 1). However, because it has been reported that the height of a plant body is decreased or increased in rice by a mutation introduced in other regions of the Della protein, it is not sufficient for an increase in plant vigor to simply introduce a mutation in the DELLA gene (Non-Patent Documents 2 and 3).

Meanwhile, the thickness of a stem, which holds a plant itself, likewise plays an important role in the heat resistance in plants and the thickening of a stem is a useful phenotype against the wilting due to the heat. In tomato, various reports have been made on the relationship between gene mutations and the expression of phenotypes but any mutation related to the phenotypic expression of increased stem diameter has not been found.

PRIOR ART DOCUMENTS

Non-Patent Documents

Non-patent Document 1: Esther Carrera et al., Plant Physiol. 2012 November; 160(3): 1581-96;
Non-patent Document 2: Non-Patent Document 2: Ko Hirano et al., Plant Cell. 2010 August; 22(8): 2680-96;
Non-patent Document 3: Non-Patent Document 3: Akira Ikeda et al., Plant Cell. 2001 May; 13(5): 999-1010.

SUMMARY OF THE INVENTION

Technical Problem

A plant carrying the mutation shown in Non-Patent Document 1 tends to have an increased plant height and a decreased stem diameter and, therefore, such a plant is considered to be vulnerable to the plant wilting due to the heat. Accordingly, there is a need for a tomato plant having an increased stem diameter as a phenotype in the cultivation of tomato in hot climate regions.

An object of the present invention is to provide a plant, such as tomato, to which the heat resistance has been imparted by increasing not only the plant height but also the stem diameter.

Technical Solution

The inventors have intensively studied to solve the above-described problem and consequently found that a plant imparted with heat resistance and having an increased stem diameter as well as an increased plant height can be obtained by allowing the plant to have a mutant Della protein in which a leucine corresponding to the leucine at position 567 in SEQ ID NO: 2 in the amino acid sequence of the Della protein has been replaced by another amino acid, and thereby completed the present invention.

That is, the present invention provides the followings.

[1] A mutant plant comprising a mutant Della protein, wherein said mutant Della protein has an amino acid sequence of a Della protein in which the leucine corresponding to leucine at position 567 in SEQ ID NO: 2 has been replaced with another amino acid.

[2] The mutant plant according to [1], wherein the mutant Della protein has an amino acid sequence of SEQ ID NO: 2 or an amino acid sequence having at least 90% identity to SEQ ID NO: 2 in which leucine at position 567 has been replaced with another amino acid.

[3] The mutant plant according to [1] or [2], wherein said another amino acid is phenylalanine.

[4] The mutant plant according to any one of [1] to [3], wherein the plant is a plant of the family Cucurbitaceae or the family Solanaceae.

[5] The mutant plant according to any one of [1] to [3], wherein the plant is tomato.

[6] A seed obtained from the mutant plant according to any one of [1] to [5].

[7] A method for producing a processed food product, comprising processing the mutant plant according to any one of [1] to [5] as a raw material into a food product.

[8] A method for producing the mutant plant, comprising cultivating the seed according to [6].

[9] A mutant della gene encoding a protein, wherein the protein has an amino acid sequence of SEQ ID NO: 2 or an amino acid sequence having at least 90% identity to SEQ ID NO: 2 in which leucine at position 567 has been replaced with another amino acid and has a function to increase the height and the stem diameter of a plant as compared to a wild type plant when the protein is carried by a plant.

[10] The mutant della gene according to [9], wherein said another amino acid is phenylalanine.

[11] A recombinant vector comprising the mutant della gene according to [9] or [10].

[12] A method for producing a mutant plant, comprising introducing the mutant della gene according to [9] or [10] into plant cells for transformation, and cultivating a regenerated plant body from the obtained transformed plant cells.

[13] The method for producing a mutant plant according to [12], wherein the mutant della gene is introduced by the recombinant vector according to [11].

[14] The method for producing a mutant plant according to [12] or [13], wherein the plant is a plant of the family Cucurbitaceae or the family Solanaceae.

[15] The method for producing a mutant plant according to [12] or [13], wherein the plant is tomato.

[16] A method for increasing the height and the stem diameter of a plant as compared to a wild type plant, comprising allowing a plant to produce the mutant Della protein according to any one of [1] to [3].

Effects of the Invention

According to the present invention, a plant in which not only an increased vigor but also the heat resistance has been imparted is obtained. Moreover, according to the present invention, such a plant exhibits significantly more excellent properties even as compared to existing mutant plants expressing altered Della proteins in the plant height, average number of fruits, fruit malformation frequency, and lycopene content, etc.

DETAILED DESCRIPTION

Figure 1:
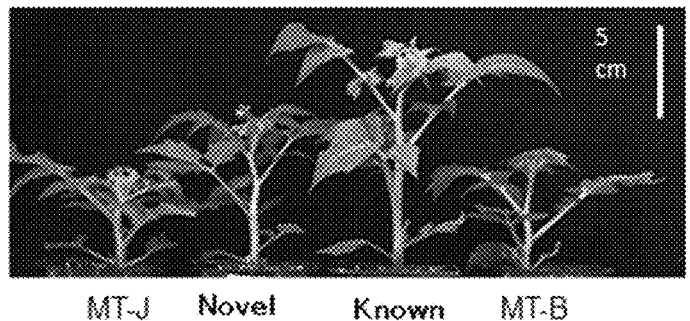
FIG. 1 is a picture of mutant tomato plants (a novel mutant of the present invention and the known procera mutant) and the wild-type tomato plants (MT-J, MT-B).

The mutant plant of the present invention is a mutant plant having a mutant Della protein in which a leucine corresponding to the leucine at position 567 in SEQ ID NO: 2 has been replaced by another amino acid in the amino acid sequence of the Della protein. The mutant plant of the present invention has such an advantage as an increased plant height as well as an increased stem diameter relative to the wild type by having such a mutant Della protein. Here, the plant height in the mutant plant of the present invention is preferably not less than 1.2 times, more preferably not less than 2 times, as large as that in the wild type. Moreover, the stem diameter in the mutant plant of the present invention is preferably not less than 1.2 times, more preferably not less than 2 times, as large as that in the wild type. The plant of the present invention also preferably exhibits the apomictic character.

Here, in terms of the plant species, a plant of the family Cucurbitaceae or the family Solanaceae is preferred. Examples of the plant of the family Solanaceae include tomato, eggplant, and potato, and a preferred plant of the family Solanaceae is tomato. Examples of the plant of the family Cucurbitaceae include cantaloupe, cucumber, melon, and watermelon.

Examples of the tomato include *Lycopersicon esculentum* (also referred to as *Solanum lycopersicum*, *Lycopersicon cerasiforme*, *Lycopersicon pimpinellifolium*, *Lycopersicon cheesmanii*, *Lycopersicon parviflorum*, *Lycopersicon chmielewskii*, *Lycopersicon hirsutum*, *Lycopersicon pennellii*, *Lycopersicon peruvianum*, *Lycopersicon chilense*, *Solanum lycopersicoides* and the like, and a preferred example is *Lycopersicon esculentum*.

The Della protein is a nuclear negative regulator for the gibberellin signaling (Plant Cell Physiol (2010) 51 (11): 1854-1868.).

For example, an example of the Della protein in tomato (*Lycopersicon esculentum*) is represented by the protein comprising the amino acid sequence of SEQ ID NO: 2.

Moreover, an example of the Della protein in cucumber (*Cucumis sativus*) is represented by the protein comprising the amino acid sequence of SEQ ID NO: 4 or SEQ ID NO: 6.

The mutant Della protein of the present invention is a protein in which a leucine corresponding to the leucine at position 567 in SEQ ID NO: 2 has been replaced by another amino acid.

Here, said another amino acid is preferably represented by aromatic amino acids (phenylalanine, tyrosine, tryptophan), and more preferably by phenylalanine.

Moreover, the mutant Della protein may contain the substitution, deletion, insertion, or addition of one or several amino acids at a position or positions except for that of the above-described substituted amino acid, as long as the mutant protein has the above-described amino acid substitution and a function to increase the plant height and the stem diameter as compared to the wild type when the protein is carried by a plant. Here, the phrase "one or several" preferably refers to a range from 1 to 20, more preferably a range from 1 to 10, and especially preferably a range from 1 to 5, though it may vary depending on the position of the amino acid residue(s) in the conformation of the protein or the type of the amino acid residue(s).

Moreover, the mutant Della protein of the present invention may have an identity above a certain level over the full-length sequence, that is, may be not less than 90%, preferably not less than 95%, and especially preferably not less than 98% identical to the amino acid sequence of SEQ ID NO: 2, as long as the mutant protein has the above-described amino acid substitution and a function to increase the plant height and the stem diameter as compared to the wild type when the protein is carried by a plant.

Additionally, in the present invention, the leucine at position 567 in SEQ ID NO: 2 refers to a position in the amino acid sequence of the tomato wild-type Della protein represented by SEQ ID NO: 2. The position of the leucine may vary depending on the amino acid deletion, insertion, or addition at a position preceding the position 567. For example, when one amino acid residue is inserted in the N-terminal region, the leucine originally at position 567 is moved to the position 568 but in such a case is referred to as a leucine corresponding to the leucine at position 567.

For example, in the case of the cucumber Della protein, as can be seen from the alignment with SEQ ID NO: 2, the leucine at position 588 in the amino acid sequence represented by SEQ ID NO: 4 or the leucine at position 570 in the amino acid sequence represented by SEQ ID NO: 6 is a leucine corresponding to the leucine at position 567 in SEQ ID NO: 2 and this leucine is replaced by another amino acid such as phenylalanine.

Additionally, a cucumber mutant Della protein may have an identity above a certain level over the full-length sequence, that is, may be not less than 90%, preferably not less than 95%, and especially preferably not less than 98% identical to the amino acid sequence of SEQ ID NO: 4 or SEQ ID NO: 6, as long as the mutant protein has the concerned mutation and a function to increase the plant height and the stem diameter as compared to the wild type when the protein is carried by a plant.

A gene encoding a mutant Della protein as described above can be obtained, for example, by introducing a mutation into the DNA encoding the wild-type Della protein, such that the mutation causes the above-described amino acid substitution to occur in the Della protein encoded by the same DNA. The mutation can systematically be introduced by the site-directed mutagenesis and the like. First, as the DNA encoding the wild-type Della protein, for example, the DNA encoding the wild-type Della protein from tomato and having the nucleotide sequence represented by SEQ ID NO: 1 or the DNA encoding the wild-type Della protein from cucumber and having the nucleotide sequence represented by SEQ ID NO: 3 or 5 may be used.

These DNA can be obtained, for example, by PCR or hybridization using oligonucleotides produced based on the sequence represented by SEQ ID NO: 1, 3 or 5.

The mutation that replaces a leucine corresponding to the leucine at position 567 in SEQ ID NO: 2 with phenylalanine is not particularly limited as long as the mutation converts the codon of the leucine to a codon of phenylalanine. For example, such a mutation is represented by an exemplary mutation that changes C to T at position 1699 in the nucleotide sequence of a gene encoding the tomato wild-type Della protein and represented by SEQ ID NO: 1. Furthermore, such a mutation is represented by an exemplary mutation that changes G to T or C at position 1764 in the nucleotide sequence of a gene encoding the cucumber wild-type Della protein and represented by SEQ ID NO: 3 or that changes C to T at position 1708 in the nucleotide sequence of a gene encoding the cucumber wild-type Della protein and represented by SEQ ID NO: 5.

Moreover, a gene encoding a mutant Della protein may be a DNA molecule which hybridizes to a DNA molecule having the nucleotide sequence of SEQ ID NO: 1 under stringent conditions, as long as the gene contains the concerned mutation and encodes a mutant Della protein having a function to increase the plant height and the stem diameter as compared to the wild type when the gene is carried by a plant. Here, the term "stringent conditions" is represented by conditions in which washing is performed at a salt concentration and temperature corresponding to those used in a typical Southern hybridization experiment, that is, at 60° C. in 0.1×SSC, 0.1% SDS, preferably at 68° C. in 0.1×SSC, 0.1% SDS, and performed once, more preferably twice or three times.

A mutant della gene as described above can be obtained by a mutagenesis technique known in the prior art. Examples of the mutagenesis technique include a method in which the wild-type DELLA gene is treated in vitro with hydroxylamine and the like; and a method in which plants carrying the wild-type DELLA gene are irradiated with ultraviolet rays or treated with a mutagen such as N-methyl-N'-nitro-N-nitrosoguanidine (NTG) or nitrous acid or EMS (ethyl methanesulfonate), which are mutagens typically used for mutagenesis. It is sufficient to analyze the sequence of the resulting della gene after mutagenesis and confirm that the gene carries the mutation (amino acid substitution).

The mutant plant of the present invention may be a natural variant carrying the above-described mutation or a variant carrying the above-described mutation as a result of mutagenesis. Furthermore, the mutant plant of the present invention can be obtained by artificially introducing a mutant della gene sequence, for example, replacing the genomic sequence with a mutant sequence or over-expressing a mutant sequence.

To obtain a plant carrying a mutant della gene by transformation, a recombinant vector including the above-described mutant della gene (DNA) is preferably used.

The vector to introduce a mutant della gene preferably includes a suitable promoter functional in plant cells and preferably a terminator. Examples of the promoter can include, but not limited to, the 35S promoter of Cauliflower mosaic virus (CaMV), the actin promoter or Elongation factor 1β promoter of rice, the ubiquitin promoter or maize, and the like.

To perform transformation of a plant such as tomato with a recombinant vector, various known methods can be used as a plant transformation method, such as *agrobacterium*-mediated transformation, electroporation, polyethylene glycol-mediated transformation, liposome-mediated transformation, particle gun bombardment and the like.

When *agrobacterium*-mediated transformation is performed, a binary vector or intermediate vector containing the T-DNA (transfer DNA) derived from the Ti plasmid or Ri plasmid of *Agrobacterium* species can be used (Nucl. Acids Res. (1984) 12(22): 8711-8721; Plasmid, (1982) 7, 15-29). The vector to be used may carry a selection marker such as hygromycin resistance or kanamycin resistance. The vector "pBI121" carrying the CaMV35S promoter and NOS terminator can be used, for example, as a vector typically used for the transformation of tomato.

Protoplasts, cultured cells, calli, and tissues, such as root, stem, leaf and seed, of a plant such as tomato can be used as a material for transformation.

When protoplasts are used, transformation can be performed by co-cultivation or fusion of these protoplasts with agrobacteria carrying a recombinant vector without or with spheroplast formation. When cultured cells are used, transformation can be performed by co-cultivation of those cultured cells with agrobacteria carrying a recombinant vector. Moreover, when a tissue is used, transformation can be performed by immersion of a section of a leaf in a suspension of agrobacteria carrying a recombinant vector for a certain time period to allow the tissue to be infected with the agrobacteria, and subsequent co-cultivation.

A plant body can be regenerated from the thus-transformed cells, callus, or tissue by a known tissue culture method.

The thus-obtained plant can be confirmed to carry a mutant della gene by a method such as gene sequencing, hybridization using a probe, and the like.

Additionally, the term "plant" in the present invention includes all of the whole plant body, an organ, a tissue, a callus, and cultured cells.

Once a plant carrying the mutation has been obtained, the mutant plant of the present invention may be plants derived from seeds thereof or may be plants obtained by crossing between those progenies and other strains. That is, once a plant carrying the mutation has been obtained, the mutant plant of the present invention may include plants in subsequent generations of the plant, the first and subsequent progeny plants derived from the crossing of those plants used as a parent, and, furthermore, plants obtained by culturing cells or tissues of those plants, as long as those plants have the above-described mutation and such characteristics as an increased plant height, an increased stem diameter and an increased heat resistance, as compared to the wild type. Those plants may include polyploid plants such as diploid and tetraploid plants.

Moreover, the present invention provides a method for producing a mutant plant, such as a mutant tomato, the method comprising the cultivation of a seed that has been obtained from the mutant plant of the present invention, such as the mutant tomato, which has such characteristics as an increased plant height, an increased stem diameter and an increased heat resistance, as compared to the wild type.

Moreover, the present invention provides a method for producing a processed food product, the method using as a raw material a mutant plant, such as a mutant tomato, which has such characteristics as an increased plant height, an increased stem diameter and an increased heat resistance, as compared to the wild type. Examples of such a product include, for example, heated products, juice, and extracts of fruits of a plant such as tomato; and, furthermore, food, food additives and the like, which contain those products.

EXAMPLES

Now, the present invention will be specifically described by way of Examples but is not limited to the following aspects.

Acquirement of a Mutant

Seeds of wild-type tomato (the wild-type Micro-Tom, MT-J) (M0) were treated with EMS (ethyl methanesulfonate) at a concentration of 1.0%. Specifically, to perform EMS treatment, 3000 seeds of the wild-type Micro-Tom (M0) were imbibed in sterilized water at normal temperature for 8 hours and subsequently immersed in 100 ml of 1.0% EMS solution with stirring for 16 hours. Mutagenized M1 seeds were recovered from the EMS solution and washed in 100 ml of sterilized water with stirring for 4 hours. After this washing step was repeated three times, the resulting M1 seeds were air-dried for several days.

About 2,000 seeds out of the air-dried M1 seeds were sown and germinated seedlings were cultured in a greenhouse. M2 seeds were obtained from each of the about 2,000 cultured M1 individual plants. Ten M2 seeds each obtained from the same M1 individual plants were similarly sown to cultivate M2 individual plants.

Out of the cultured M2 individual plants, a line exhibiting apomixis was isolated and named E2753 mutant.

Various gene sequences were analyzed in this E2753 mutant and it was found that the gene encoding the Della protein carried a mutation that replaced the leucine at position 567 in the Della protein with phenylalanine (a mutation that changed C to T at position 1699 in the nucleotide sequence of SEQ ID NO: 1).

Example 1: Evaluation of the Apomictic Character

Micro-Tom (MT)-J, Micro-Tom (MT)-B, the mutant of the present invention and a known mutant were cultivated from seeds thereof and their apomictic characters were evaluated based on the number of fruiting flowers divided by the number of flowers with stamen removed.

The result is shown in Table 1. This indicated that the mutant of the present invention exhibited the apomictic character at a level similar to that of the known mutant.

TABLE 1

| Frequency of apomixes | |
|---|---|
| | No. of fruiting flower/No. of flowers with stamen removed (Fruit production rate, %) |
| Micro-Tom (MT)-J | 0/14 (0%) |
| Mutant of the present invention[a] | 15/20 (75%) |
| Micro-Tom (MT)-B | 1/22 (5%) |
| Known mutant[b] | 25/31 (81%) |

[a]E2753 mutant
[b]Mutant described in Non-Patent Document 1, in which the valine at position 302 has been replaced with glutamic acid (procera).

Next, Micro-Tom (MT)-J, Micro-Tom (MT)-B, the mutant of the present invention and the known mutant were cultivated from seeds thereof and the plant height (the height to the first flower) and the stem diameter were measured 30 days later.

The result is shown in FIG. 1 and Table 2.

TABLE 2

| | Height to the first flower (cm) | Stem diameter of the fifth internode (mm) |
|---|---|---|
| MT-J | 5.0 | 3.9 |
| E2753 | 8.7 | 5.4 |
| MT-B | 7.5 | 4.3 |
| procera | 11.9 | 4.0 |

Consequently, the mutant having the mutation, which replaces the leucine at position 567 of the Della protein with phenylalanine, was found to have a greater plant height and a larger stem diameter than the wild type. Since the character of the increased stem diameter was not observed in the known mutant, the L567F mutation was found to be a very useful mutation.

Example 2: Comparison of Growth and Productivity Under Greenhouse Cultivation in Midsummer In greenhouse cultivation in midsummer, the pollination in the wild type (WT) is inhibited by heat stress so that the yield is greatly decreased. Then, the above-described influence of the heat stress was evaluated in the mutant (E2753) carrying a mutation that replaced the leucine at position 567 of the Della protein with phenylalanine and in the mutant (procera) carrying a mutation that replaced the valine at position 302 of the Della protein with glutamic acid. M4 plants of the E2753 mutant obtained in the above-described Example 1 were back-crossed with WT (Micro-Tom (MT)-B) and the plants derived therefrom in the generation suitable for the analysis was used as E2753 mutant plants.

Figure 2:
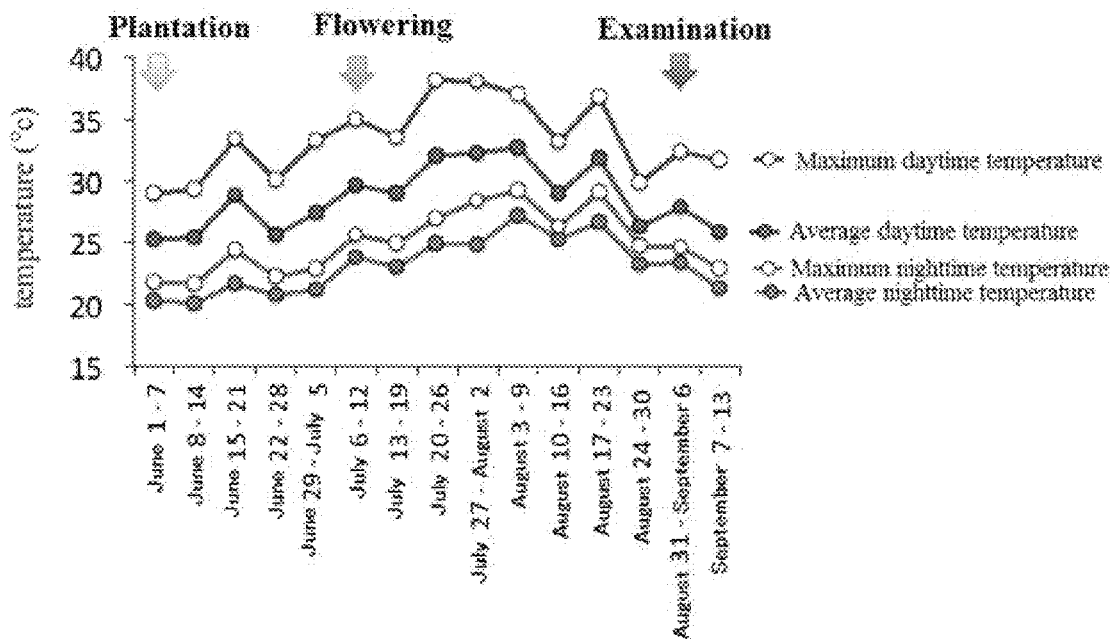
FIG. 2 depicts the overview of a cultivation schedule to compare the growth and the productivity under greenhouse cultivation in midsummer and the temperature during the cultivation period.

The greenhouse cultivation in midsummer, which is a condition for heat stress, was performed according to a schedule in which WT (Micro-Tom (MT)-B), E2753 and procera plants were planted in June and afterwards pollinated by applying vibration to the plants around three times a week and examined for the growth, the productivity and the like from the end of August to the beginning of September. Individual plants of all the lines flowered in the same week of July. The overview of the cultivation schedule and the temperature in the greenhouse in the period from the plantation to the examination are shown in FIG. 2.

Figure 5:
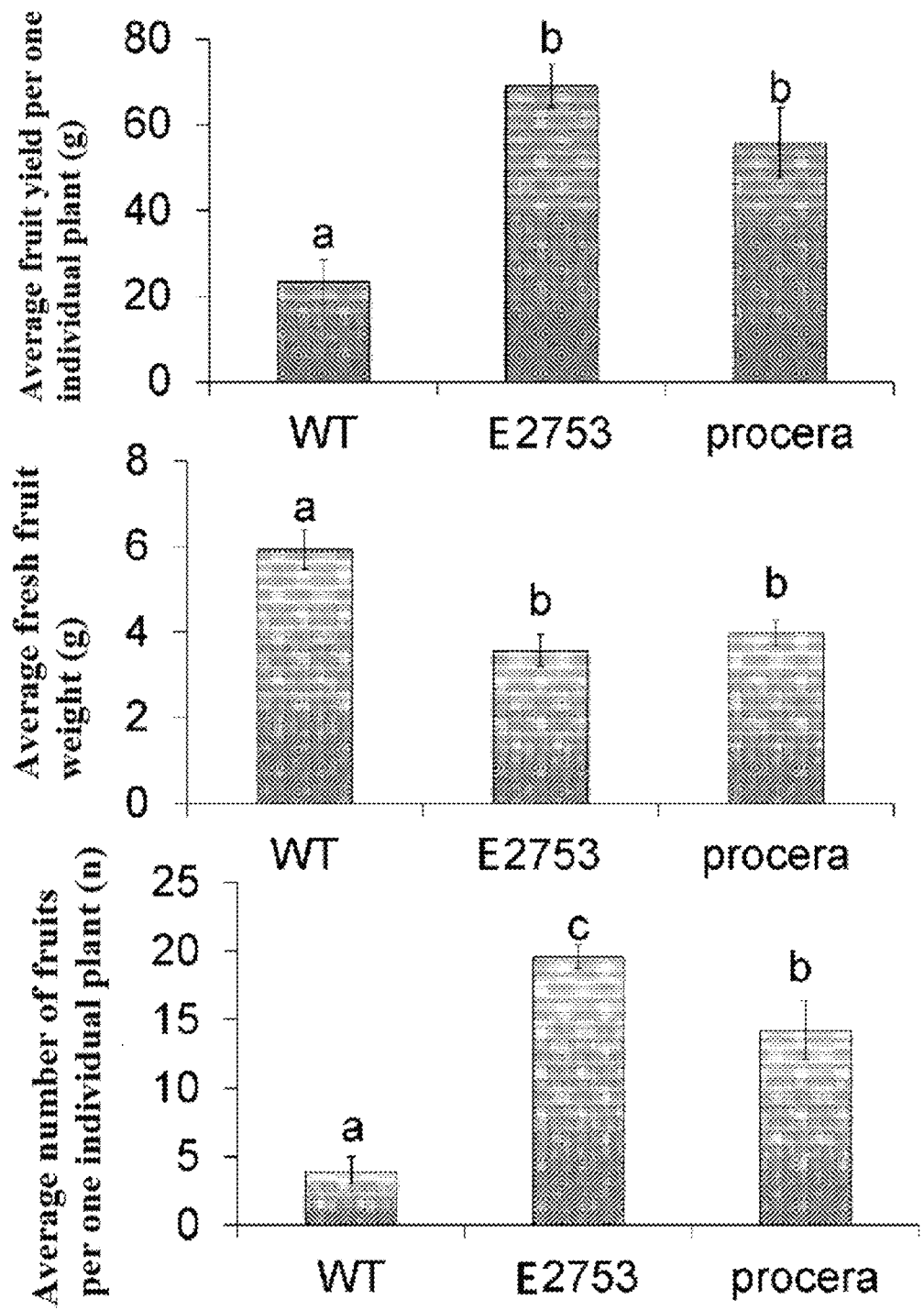
FIG. 5 shows graphs indicating the average fruit yield, the average fresh fruit weight, and the average number of fruits in each of WT, E2753 and procera under greenhouse cultivation in midsummer. The different alphabets "a", "b", and "c" in the table indicate a significant difference (P<0.05) among them in the Student's t-test.
Figure 6:
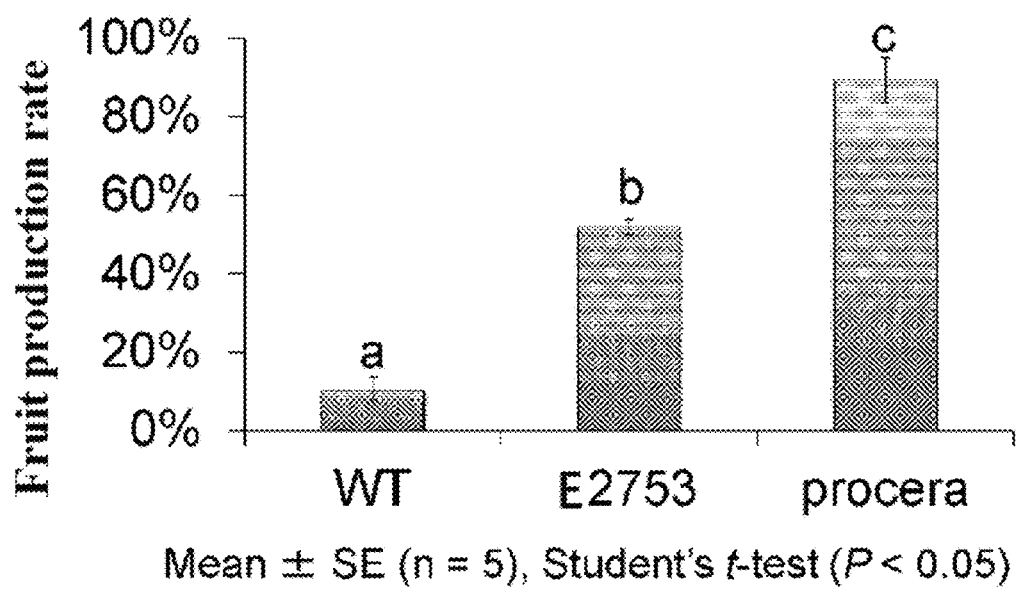
FIG. 6 shows a graph indicating the fruit production rate in each of WT, E2753 and procera under greenhouse cultivation in midsummer. The different alphabets "a", "b", and "c" in the table indicate a significant difference (P<0.05) among them in the Student's t-test.
Figure 7:
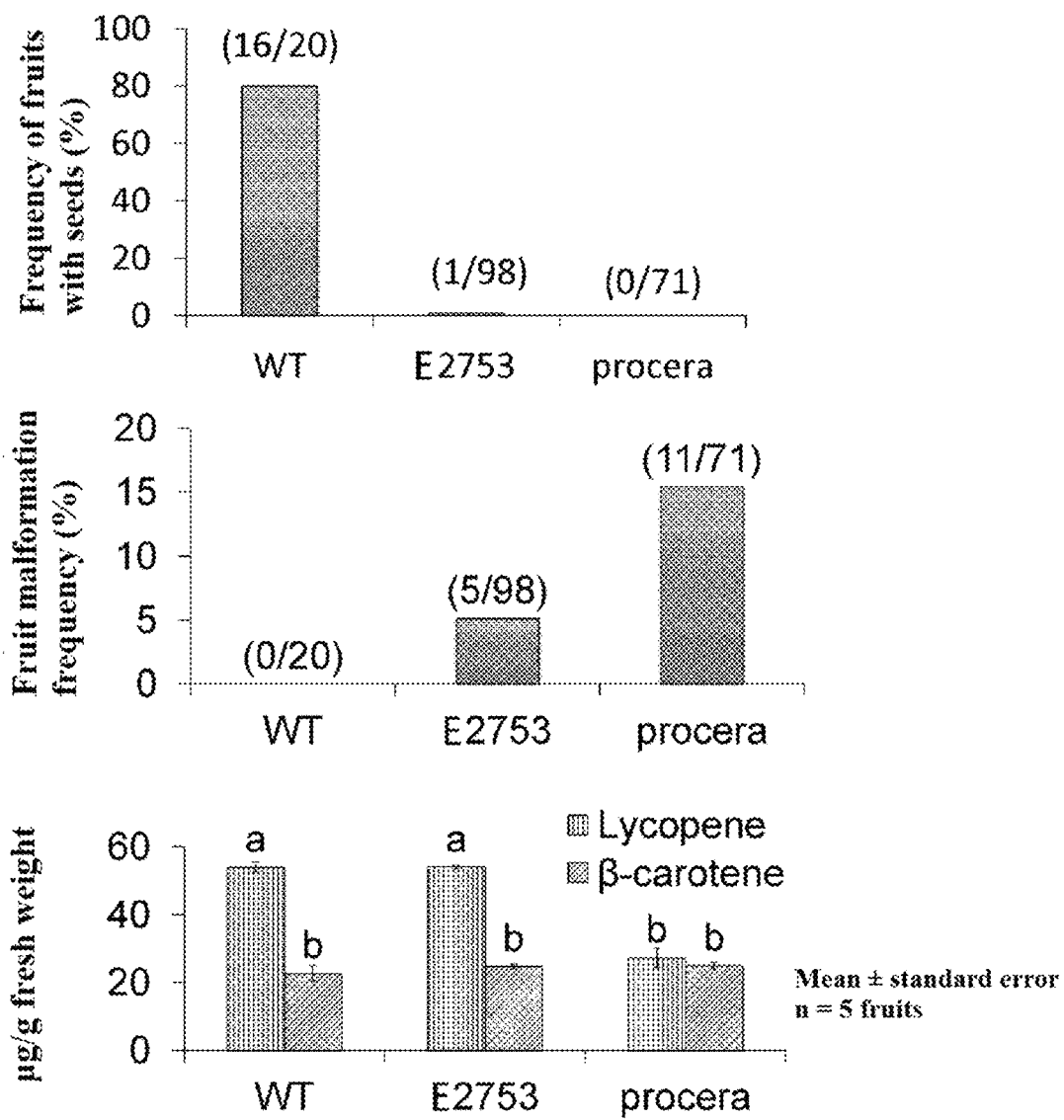
FIG. 7 shows graphs indicating the frequency of fruits with seeds, the fruit malformation frequency, and the μg/g fresh weight in each of WT, E2753 and procera under greenhouse cultivation in midsummer. The different alphabets "a" and "b" in the table indicate a significant difference (P<0.05) between them in the Student's t-test.

The results of the evaluation are shown in FIGS. 3 to 7 and Table 3 below.

average fresh fruit weight in E2753 was less than that in WT and as much as that in procera (FIG. 5). The average number of fruits per one individual plant in E2753 was significantly more than that in WT and procera (FIG. 5). Moreover, when the fruit production rate was calculated by dividing the number of fruits including immatures by the total flower number during the cultivation period, the fruit production rate in E2753 was higher than that in WT but lower than that in procera (FIG. 6). The frequency of fruits with seeds in E2753 was lower than that in WT and as high as that in procera (FIG. 7). The fruit malformation frequency in E2753 was higher than that in WT but lower than that in procera (FIG. 7). Furthermore, the severity of malformation in procera was larger than that in E2753. The lycopene content contained in E2753 was as much as that in WT and significantly more than that in procera (FIG. 7). This result consisted with the coloring defects in many fruits of procera during the phenotypic observation of the appearance of the fruits.

As described above, E2753 exhibited significantly excellent properties in the plant height, average number of fruits, fruit malformation frequency, and lycopene content, etc as compared to not only WT but also procera.

TABLE 3

|  | WT | e2753 | procera |
|---|---|---|---|
| Plant height (cm) | 11.8 ± 0.3  a | 15.2 ± 0.5  b | 17.9 ± 0.8  c |
| Number of leaves at the flowering time (n) | 0.8 ± 0.0  a | 9.8 ± 0.4  b | 9.3 ± 0.3  b |
| Stem diameter (mm) | 7.0 ± 0.1  a | 7.5 ± 0.1  b | 6.6 ± 0.2  a |
| Fresh weight of the ground part (g) | 46.1 ± 2.9  a | 38.3 ± 2.2  a | 27.7 ± 1.7  b |
| Dryroot weight (g) | 0.39 ± 0.06  a | 0.27 ± 0.03  b | 0.23 ± 0.02  b |
| Total flower number per one individual plant (n) | 95.0 ± 8.5  a | 52.2 ± 5.5  b | 23.5 ± 2.2  c |
| Average fruit yield per one individual plant (g) | 23.3 ± 5.1  a | 69.0 ± 5.1  b | 55.7 ± 8.3  b |
| Average fresh fruit weight (g) | 5.9 ± 0.5  a | 3.3 ± 0.3  b | 3.8 ± 0.2  b |
| Average number of fruits per one individual plant (n) | 4.0 ± 1.0  a | 19.6 ± 0.9  c | 14.3 ± 2.2  b |
| Fruit production rate (%) | 10.4 ± 3.3  a | 51.8 ± 1.9  b | 89.2 ± 5.8  c |
| Mean ± standard error of five plants from each line | | | |
| Frequency of fruits with seeds (%)[1] | 80.0 | 1.0 | 0.0 |
| Fruit malformation frequency (%)[1] | 0.0 | 5.1 | 15.4 |
| Lycopene content (μg/g fresh weight)[2] | 54.0 ± 1.4  a | 54.0 ± 0.4  a | 27.3 ± 2.8  b |
| β-carotene content (μg/g fresh weight)[2] | 22.7 ± 2.2  a | 24.8 ± 0.8  a | 25.0 ± 1.0  a |

Figure 3:
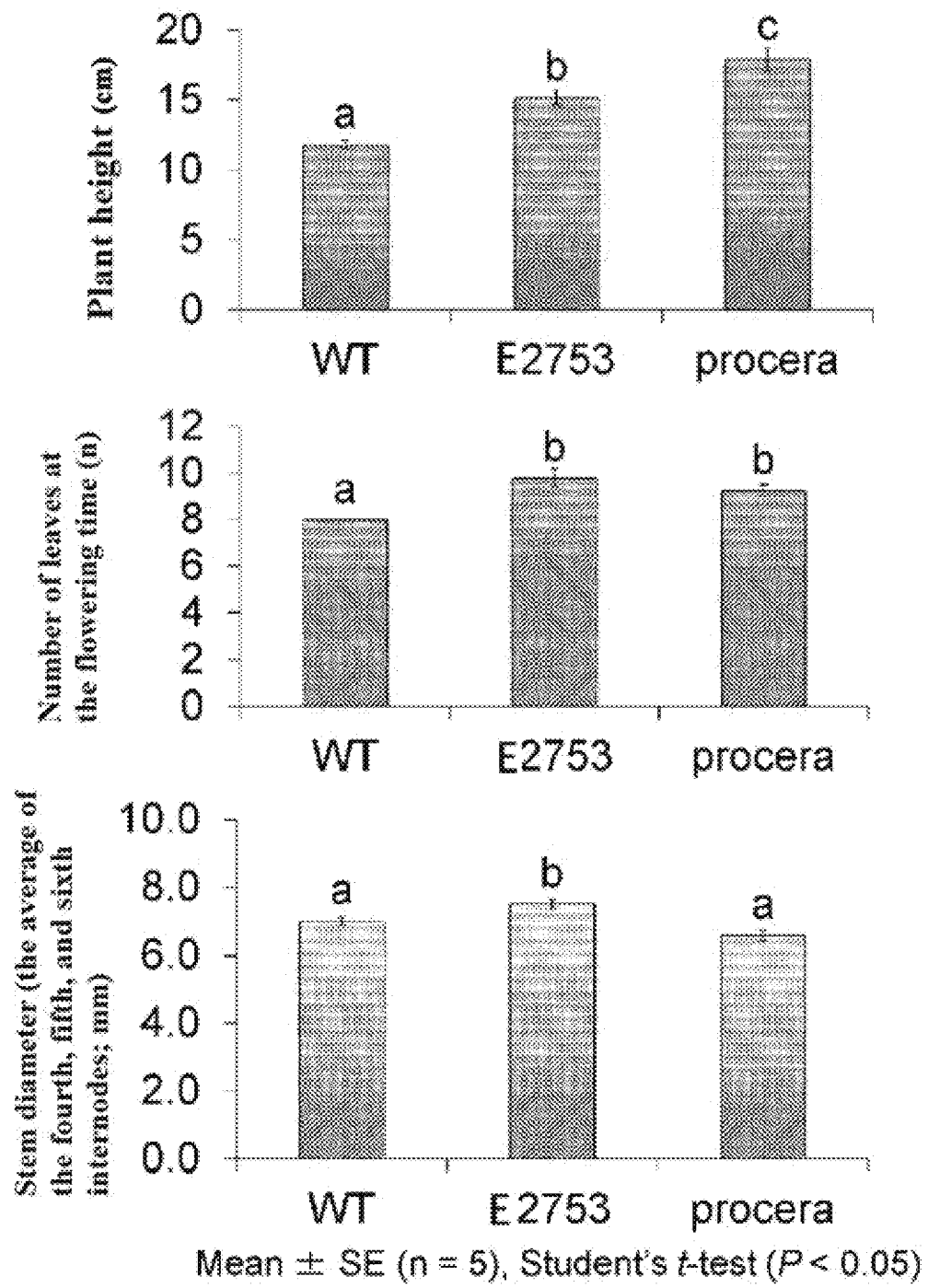
FIG. 3 shows graphs indicating the plant height, the number of leaves at the flowering time, and the stem diameter in each of WT, E2753 and procera under greenhouse cultivation in midsummer. The different alphabets "a", "b", and "c" in the table indicate a significant difference (P<0.05) among them in the Student's t-test.
Figure 4:
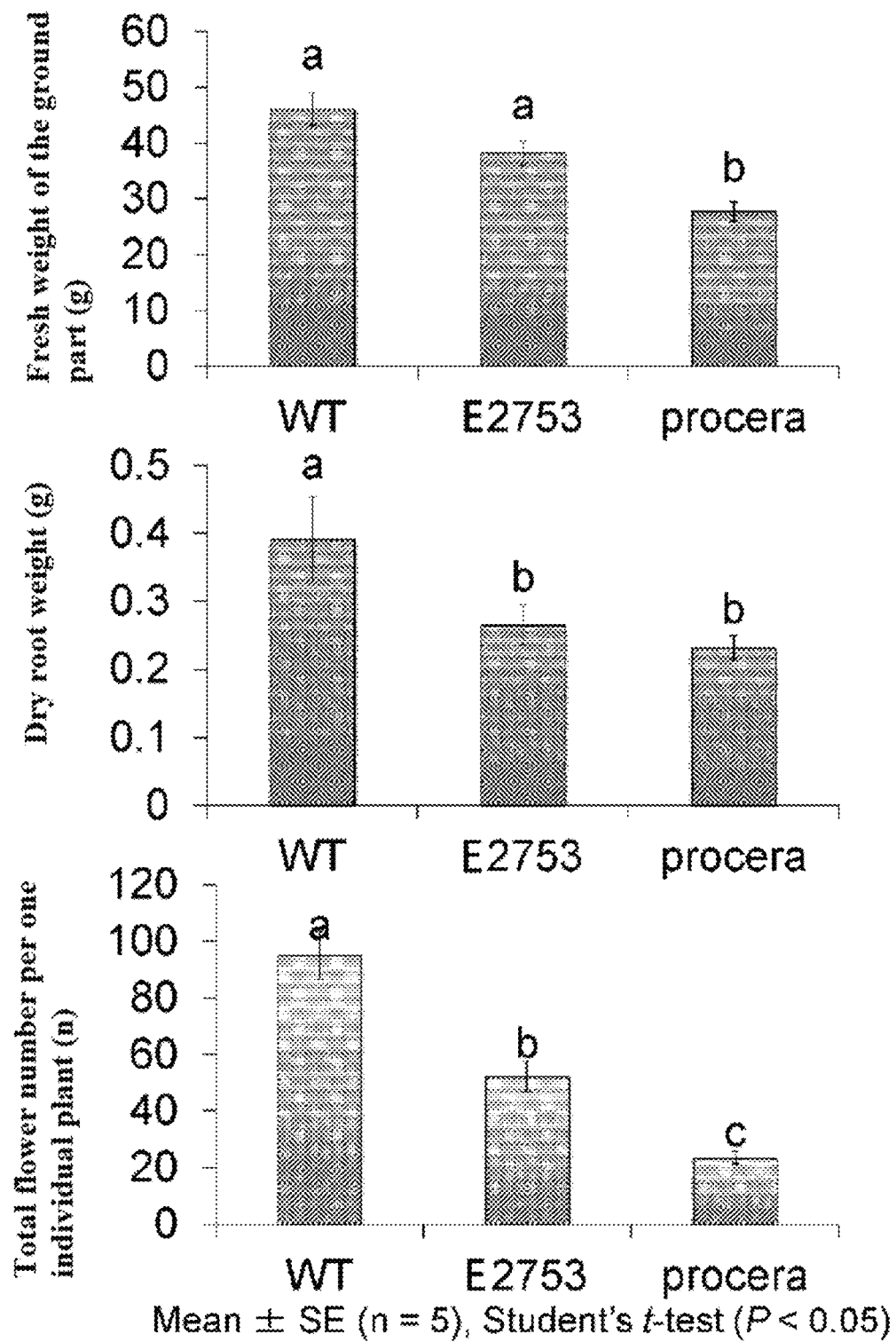
FIG. 4 shows graphs indicating the fresh weight of the ground part, the dry root weight, and the total flower number per one individual plant in each of WT, E2753 and procera under greenhouse cultivation in midsummer. The different alphabets "a", "b", and "c" in the table indicate a significant difference (P<0.05) among them in the Student's t-test.

The different alphabets (a, b, and c) in the table indicate a significant difference (P < 0.05) among them in the Student's t-test
[1] in total fruits from 5 individual plants in each line (WT, 20; E2753, 90; pro, 71)
[2] in 5 fruits The plant height in E2753 is greater than that in WT and smaller than that in procera (FIG. 3). Because extensive elongation of the plant height tends to be undesired in the cultivation of an ordinary tomato, E2753 can be considered to have a more excellent property in this regard than procera. The number of leaves at the flowering time in E2753 was more than that in WT and fewer than that in procera but the difference from that in procera was not significant (FIG. 3). The stem diameter in E2753 was larger than that in WT and procera (FIG. 3). The fresh weight of the ground part in E2753 was less than that in WT and more than that in procera but there was no statistically significant difference from that in WT (FIG. 4). The dry root weight in E2753 was less than that in WT but as much as that in procera (FIG. 4). The total flower number per one individual plant in E2753 was fewer than that in WT and more than that in procera (FIG. 4). The average fruit yield per one individual plant in E2753 was more than that in WT and procera but there was no significant difference from that in procera (FIG. 5). The Example 3: Evaluation of the Sensitivity to a Gibberellin Biosynthesis Inhibitor The sensitivity to a gibberellin biosynthesis inhibitor was evaluated in WT (Micro-Tom (MT)-B), E2753 and procera. The same E2753 plants as used in Example 2 were used as E2753 mutant plants.

Two days after starting the imbibition, the above-described three types of plants were transferred onto MS medium containing a gibberellin biosynthesis inhibitor, paclobutrazol (PAC), and the stem length was measured 10 days later.

Figure 8:
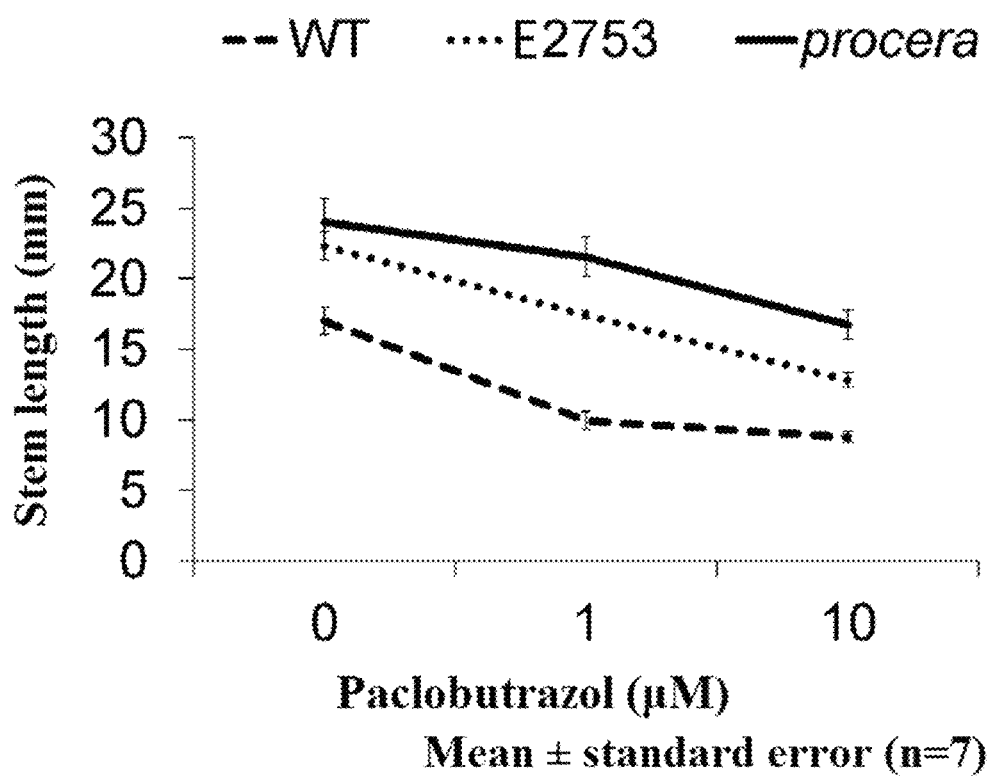
FIG. 8 shows a graph indicating the sensitivity to paclobutrazol in each of WT, E2753 and procera.

The result of the measurement is shown in FIG. 8. As shown in FIG. 8, the stem length in E2753 was longer than that in WT and shorter than that in procera. Accordingly, E2753 can be considered to have exhibited a sensitivity level lower than that in WT and higher than that in procera.

Loss-of-function mutants of Della, which is an inhibitor for the gibberellin signaling pathway, are considered to be insusceptible to the inhibition of the gibberellin biosynthesis (to be less sensitive to PAC) because the gibberellin signaling is constitutively activated in the mutants as well as in procera and E2753. From the above result, E2753 is considered to be a mutant more suitable for practical use as compared to procera because the mutation in the latter causes an excessively strong phenotype, which is less practical, in contrast to the mutation in the former, which causes a milder phenotype.

Example 4: Comparison of Seed Production

Seed production was compared in WT (Micro-Tom (MT)-B), E2753 and procera. The same E2753 plants as used in Example 2 were used as E2753 mutant plants.

The above-described three types of plants were cultivated in a culture room (daytime/nighttime=25° C., 16 hours/20° C., 8 hours) and 10 flowers each from the plants were pollinated by directly depositing pollen onto stigmas, and the number of seeds per produced fruit was determined.

Figure 9:
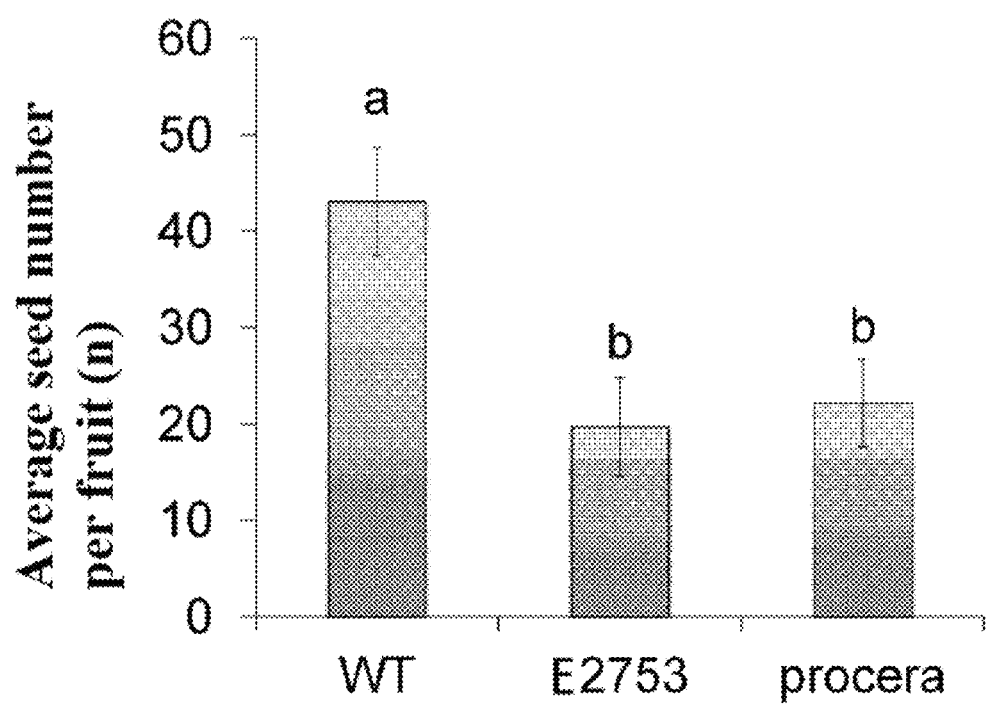
FIG. 9 shows a graph indicating the average seed number per fruit in each of WT, E2753 and procera. The different alphabets "a" and "b" in the table indicate a significant difference (P<0.05) between them in the Student's t-test.

The result is shown in FIG. 9 and Table 4 below.

TABLE 4

| WT | 43.1 ± 5.6 a |
|---|---|
| E2753 | 19.7 ± 5.1 a |
| procera | 22.2 ± 4.6 b |

The different alphabets "a" and "b" indicate a significant difference (P < 0.05) between them in the Student's t-test.

E2753 demonstrated a seed production level approximately a half as high as that in WT and as high as that in procera.

What is claimed is:

1. A mutant plant comprising a mutant Della protein, wherein said mutant Della protein has an amino acid sequence of a Della protein having at least 95% identity to SEQ ID NO: 2 in which the leucine corresponding to leucine at position 567 in SEQ ID NO: 2 has been replaced with phenylalanine.

2. The mutant plant according to claim 1, wherein the mutant Della protein has an amino acid sequence having at least 98% identity to SEQ ID NO: 2 in which leucine at position 567 has been replaced with phenylalanine.

3. The mutant plant according to claim 1, wherein the plant is a plant of the family Cucurbitaceae or the family Solanaceae.

4. The mutant plant according to claim 1, wherein the plant is tomato.

5. A seed obtained from the mutant plant according to claim 1, wherein said seed comprises a Della protein having at least 95% identity to SEQ ID NO: 2 in which the leucine corresponding to leucine at position 567 in SEQ ID NO: 2 has been replaced with phenylalanine.

6. A method for producing a processed food product, comprising processing the mutant plant according to claim 1 as a raw material into a food product.

7. A method for producing the mutant plant, comprising cultivating the seed according to claim 6.

8. A method for increasing the height and the stem diameter of a plant as compared to a wild type plant, comprising allowing a plant to produce the mutant Della protein according to claim 1.

* * * * *

SEQUENCE LISTING

<160> NUMBER OF SEQ ID NOS: 6

<210> SEQ ID NO 1
<211> LENGTH: 1767
<212> TYPE: DNA
<213> ORGANISM: Solanum lycopersicum
<220> FEATURE:
<221> NAME/KEY: CDS
<222> LOCATION: (1)..(1764)

<400> SEQUENCE: 1

```
atg aag aga gat cga gat cga gat cga gaa aga gag aaa aga gca ttc     48
Met Lys Arg Asp Arg Asp Arg Asp Arg Glu Arg Glu Lys Arg Ala Phe
1               5                   10                  15 tct aat ggt gct gtt tct tca ggg aaa agt aag att tgg gaa gaa gat     96
Ser Asn Gly Ala Val Ser Ser Gly Lys Ser Lys Ile Trp Glu Glu Asp
            20                  25                  30 gaa gaa gaa aaa cca gat gct gga atg gat gag ctt tta gct gtt ttg    144
Glu Glu Glu Lys Pro Asp Ala Gly Met Asp Glu Leu Leu Ala Val Leu
        35                  40                  45 ggt tat aaa gtg aag tcg tct gat atg gcg gat gtt gct caa aaa ctt    192
Gly Tyr Lys Val Lys Ser Ser Asp Met Ala Asp Val Ala Gln Lys Leu
    50                  55                  60 gaa cag ctt gag atg gct atg ggt aca acg atg gaa gat ggt att act    240
Glu Gln Leu Glu Met Ala Met Gly Thr Thr Met Glu Asp Gly Ile Thr
65                  70                  75                  80 cat ctt tct act gat acc gtt cat aaa aac cca tct gat atg gct ggt    288
His Leu Ser Thr Asp Thr Val His Lys Asn Pro Ser Asp Met Ala Gly
                85                  90                  95 tgg gta caa agt atg tta tct tcg att tcg aca aac ttt gat atg tgt    336
Trp Val Gln Ser Met Leu Ser Ser Ile Ser Thr Asn Phe Asp Met Cys
            100                 105                 110 aat cag gaa aac gat gtg ctt gta tct ggt tgt ggt tct tct tct tct    384
Asn Gln Glu Asn Asp Val Leu Val Ser Gly Cys Gly Ser Ser Ser Ser
        115                 120                 125 ata atc gat ttc tca caa aat cat cga aca agt acc att tct gat gat    432
Ile Ile Asp Phe Ser Gln Asn His Arg Thr Ser Thr Ile Ser Asp Asp
    130                 135                 140 gat tta aga gct ata cct ggt ggt gct gtt ttc aat tcg gat agt aat    480
Asp Leu Arg Ala Ile Pro Gly Gly Ala Val Phe Asn Ser Asp Ser Asn
145                 150                 155                 160 aaa aga cac aga tca aca act tct agt ttt tca act aca tcc tca tct    528
Lys Arg His Arg Ser Thr Thr Ser Ser Phe Ser Thr Thr Ser Ser Ser
                165                 170                 175 atg gtg aca gat tca tca gca acg aga cct gtt gta cta gtt gat tca    576
```

```
                Met Val Thr Asp Ser Ser Ala Thr Arg Pro Val Val Leu Val Asp Ser
                            180                 185                 190 caa gaa act ggg gtt cgt ctt gtt cat act tta atg gcg tgt gct gaa          624
Gln Glu Thr Gly Val Arg Leu Val His Thr Leu Met Ala Cys Ala Glu
            195                 200                 205 gct gta caa caa gaa aat tta act tta gcg gat caa ctt gtt aga cat          672
Ala Val Gln Gln Glu Asn Leu Thr Leu Ala Asp Gln Leu Val Arg His
        210                 215                 220 att ggt att ctt gcg gtt tca caa tct ggt gct atg aga aaa gtt gct          720
Ile Gly Ile Leu Ala Val Ser Gln Ser Gly Ala Met Arg Lys Val Ala
225                 230                 235                 240 act tac ttt gct gaa gca tta gca aga aga atc tac aaa att tat cca          768
Thr Tyr Phe Ala Glu Ala Leu Ala Arg Arg Ile Tyr Lys Ile Tyr Pro
            245                 250                 255 caa gat tca atg gaa tca tca tat aca gat gtt tta caa atg cat ttc          816
Gln Asp Ser Met Glu Ser Ser Tyr Thr Asp Val Leu Gln Met His Phe
        260                 265                 270 tat gaa act tgc cct tat ctc aaa ttc gct cat ttt act gct aat caa          864
Tyr Glu Thr Cys Pro Tyr Leu Lys Phe Ala His Phe Thr Ala Asn Gln
    275                 280                 285 gcc att ctt gaa gcg ttt aca ggt tgt aac aaa gtt cat gta att gat          912
Ala Ile Leu Glu Ala Phe Thr Gly Cys Asn Lys Val His Val Ile Asp
290                 295                 300 ttc agc tta aaa cag ggt atg caa tgg cct gca ctt atg caa gct tta          960
Phe Ser Leu Lys Gln Gly Met Gln Trp Pro Ala Leu Met Gln Ala Leu
305                 310                 315                 320 gct tta cgc ccc ggt gga cct ccg gca ttt aga ctc acc gga atc gga         1008
Ala Leu Arg Pro Gly Gly Pro Pro Ala Phe Arg Leu Thr Gly Ile Gly
            325                 330                 335 cct cca cag ccg gat aac aca gat gcc ttg caa caa gtt gga tgg aag         1056
Pro Pro Gln Pro Asp Asn Thr Asp Ala Leu Gln Gln Val Gly Trp Lys
        340                 345                 350 ttg gct cag tta gcg gaa act att ggg gtt gaa ttt gaa ttc agg gga         1104
Leu Ala Gln Leu Ala Glu Thr Ile Gly Val Glu Phe Glu Phe Arg Gly
    355                 360                 365 ttt gtt gct aat tcg tta gca gat ctt gat gcg act ata ctt gat ata         1152
Phe Val Ala Asn Ser Leu Ala Asp Leu Asp Ala Thr Ile Leu Asp Ile
370                 375                 380 agg cca agt gaa act gaa gca gta gct ata aac tct gtt ttt gag ctt         1200
Arg Pro Ser Glu Thr Glu Ala Val Ala Ile Asn Ser Val Phe Glu Leu
385                 390                 395                 400 cat cga ttg tta tcc cgg ccg gga gca att gaa aaa gtg ttg aac tct         1248
His Arg Leu Leu Ser Arg Pro Gly Ala Ile Glu Lys Val Leu Asn Ser
            405                 410                 415 att aaa cag att aac ccg aag att gtt act ctt gtt gag caa gaa gcg         1296
Ile Lys Gln Ile Asn Pro Lys Ile Val Thr Leu Val Glu Gln Glu Ala
        420                 425                 430 aat cat aac gca ggg gtt ttt att gat aga ttt aac gaa gct ttg cat         1344
Asn His Asn Ala Gly Val Phe Ile Asp Arg Phe Asn Glu Ala Leu His
    435                 440                 445 tat tac tca acc atg ttt gat tcg tta gaa agc tct ggg tct tcg tct         1392
Tyr Tyr Ser Thr Met Phe Asp Ser Leu Glu Ser Ser Gly Ser Ser Ser
450                 455                 460 tca gct tca cca act ggg att ctt cct caa cct ccg gtg aac aat caa         1440
Ser Ala Ser Pro Thr Gly Ile Leu Pro Gln Pro Pro Val Asn Asn Gln
465                 470                 475                 480 gat ttg gtg atg tcg gag gtt tat tta ggg aga cag att tgt aac gtg         1488
Asp Leu Val Met Ser Glu Val Tyr Leu Gly Arg Gln Ile Cys Asn Val
            485                 490                 495
```

```
gtg gct tgt gaa ggt tca gat cga gtt gaa cga cat gaa aca ctg aat    1536
Val Ala Cys Glu Gly Ser Asp Arg Val Glu Arg His Glu Thr Leu Asn
            500                 505                 510 caa tgg agg gtt agg atg aac tca tct ggg ttc gat ccg gtt cat ctg    1584
Gln Trp Arg Val Arg Met Asn Ser Ser Gly Phe Asp Pro Val His Leu
        515                 520                 525 ggt tca aat gcg ttc aaa caa gct tcc atg ctt tta gct ctg ttc gcc    1632
Gly Ser Asn Ala Phe Lys Gln Ala Ser Met Leu Leu Ala Leu Phe Ala
    530                 535                 540 ggc ggc gat ggt tac agg gtg gaa gaa aac gat ggg tgt ctt atg ttg    1680
Gly Gly Asp Gly Tyr Arg Val Glu Glu Asn Asp Gly Cys Leu Met Leu
545                 550                 555                 560 ggg tgg cat aca cgg cca ctt ata gct acc tcc gcc tgg aag cta ttg    1728
Gly Trp His Thr Arg Pro Leu Ile Ala Thr Ser Ala Trp Lys Leu Leu
                565                 570                 575 ccg gac tcc ggc acc ggc gcc gga gaa gtc gag ttg taa                1767
Pro Asp Ser Gly Thr Gly Ala Gly Glu Val Glu Leu
            580                 585
```

<210> SEQ ID NO 2
<211> LENGTH: 588
<212> TYPE: PRT
<213> ORGANISM: Solanum lycopersicum

<400> SEQUENCE: 2

```
Met Lys Arg Asp Arg Asp Arg Asp Arg Glu Arg Glu Lys Arg Ala Phe
1               5                   10                  15

Ser Asn Gly Ala Val Ser Ser Gly Lys Ser Lys Ile Trp Glu Glu Asp
            20                  25                  30

Glu Glu Glu Lys Pro Asp Ala Gly Met Asp Glu Leu Leu Ala Val Leu
        35                  40                  45

Gly Tyr Lys Val Lys Ser Ser Asp Met Ala Asp Val Ala Gln Lys Leu
    50                  55                  60

Glu Gln Leu Glu Met Ala Met Gly Thr Thr Met Glu Asp Gly Ile Thr
65                  70                  75                  80

His Leu Ser Thr Asp Thr Val His Lys Asn Pro Ser Asp Met Ala Gly
                85                  90                  95

Trp Val Gln Ser Met Leu Ser Ser Ile Ser Thr Asn Phe Asp Met Cys
            100                 105                 110

Asn Gln Glu Asn Asp Val Leu Val Ser Gly Cys Gly Ser Ser Ser Ser
        115                 120                 125

Ile Ile Asp Phe Ser Gln Asn His Arg Thr Ser Thr Ile Ser Asp Asp
    130                 135                 140

Asp Leu Arg Ala Ile Pro Gly Gly Ala Val Phe Asn Ser Asp Ser Asn
145                 150                 155                 160

Lys Arg His Arg Ser Thr Thr Ser Ser Phe Ser Thr Thr Ser Ser Ser
                165                 170                 175

Met Val Thr Asp Ser Ser Ala Thr Arg Pro Val Val Leu Val Asp Ser
            180                 185                 190

Gln Glu Thr Gly Val Arg Leu Val His Thr Leu Met Ala Cys Ala Glu
        195                 200                 205

Ala Val Gln Gln Glu Asn Leu Thr Leu Ala Asp Gln Leu Val Arg His
    210                 215                 220

Ile Gly Ile Leu Ala Val Ser Gln Ser Gly Ala Met Arg Lys Val Ala
225                 230                 235                 240

Thr Tyr Phe Ala Glu Ala Leu Ala Arg Arg Ile Tyr Lys Ile Tyr Pro
                245                 250                 255
```

Gln Asp Ser Met Glu Ser Ser Tyr Thr Asp Val Leu Gln Met His Phe
            260                 265                 270

Tyr Glu Thr Cys Pro Tyr Leu Lys Phe Ala His Phe Thr Ala Asn Gln
        275                 280                 285

Ala Ile Leu Glu Ala Phe Thr Gly Cys Asn Lys Val His Val Ile Asp
    290                 295                 300

Phe Ser Leu Lys Gln Gly Met Gln Trp Pro Ala Leu Met Gln Ala Leu
305                 310                 315                 320

Ala Leu Arg Pro Gly Pro Pro Ala Phe Arg Leu Thr Gly Ile Gly
            325                 330                 335

Pro Pro Gln Pro Asp Asn Thr Asp Ala Leu Gln Gln Val Gly Trp Lys
            340                 345                 350

Leu Ala Gln Leu Ala Glu Thr Ile Gly Val Glu Phe Glu Phe Arg Gly
        355                 360                 365

Phe Val Ala Asn Ser Leu Ala Asp Leu Asp Ala Thr Ile Leu Asp Ile
    370                 375                 380

Arg Pro Ser Glu Thr Glu Ala Val Ala Ile Asn Ser Val Phe Glu Leu
385                 390                 395                 400

His Arg Leu Leu Ser Arg Pro Gly Ala Ile Glu Lys Val Leu Asn Ser
            405                 410                 415

Ile Lys Gln Ile Asn Pro Lys Ile Val Thr Leu Val Glu Gln Glu Ala
            420                 425                 430

Asn His Asn Ala Gly Val Phe Ile Asp Arg Phe Asn Glu Ala Leu His
        435                 440                 445

Tyr Tyr Ser Thr Met Phe Asp Ser Leu Glu Ser Gly Ser Ser Ser
    450                 455                 460

Ser Ala Ser Pro Thr Gly Ile Leu Pro Gln Pro Pro Val Asn Asn Gln
465                 470                 475                 480

Asp Leu Val Met Ser Glu Val Tyr Leu Gly Arg Gln Ile Cys Asn Val
            485                 490                 495

Val Ala Cys Glu Gly Ser Asp Arg Val Glu Arg His Glu Thr Leu Asn
            500                 505                 510

Gln Trp Arg Val Arg Met Asn Ser Ser Gly Phe Asp Pro Val His Leu
        515                 520                 525

Gly Ser Asn Ala Phe Lys Gln Ala Ser Met Leu Leu Ala Leu Phe Ala
530                 535                 540

Gly Gly Asp Gly Tyr Arg Val Glu Glu Asn Asp Gly Cys Leu Met Leu
545                 550                 555                 560

Gly Trp His Thr Arg Pro Leu Ile Ala Thr Ser Ala Trp Lys Leu Leu
            565                 570                 575

Pro Asp Ser Gly Thr Gly Ala Gly Glu Val Glu Leu
            580                 585

<210> SEQ ID NO 3
<211> LENGTH: 1794
<212> TYPE: DNA
<213> ORGANISM: Cucumis sativus
<220> FEATURE:
<221> NAME/KEY: CDS
<222> LOCATION: (1)..(1791)

<400> SEQUENCE: 3 atg aag cgg gag ctt gaa gat gat aga tct act acc cct ggg gat gcc    48
Met Lys Arg Glu Leu Glu Asp Asp Arg Ser Thr Thr Pro Gly Asp Ala
1               5                   10                  15

| | | |
|---|---|---|
| ccg agg att gtg aag gga gat tct tct tca atg tcg tct gga aaa ctc<br>Pro Arg Ile Val Lys Gly Asp Ser Ser Ser Met Ser Ser Gly Lys Leu<br>20 25 30 | | 96 |
| aag atg tgg cag ccc cat gag gag gac gag ggg aag gat gcc aaa gac<br>Lys Met Trp Gln Pro His Glu Glu Asp Glu Gly Lys Asp Ala Lys Asp<br>35 40 45 | | 144 |
| ggc gcc gcc ggt gga atg gat gag ttg ctt gct gtt ttg ggt tac aag<br>Gly Ala Ala Gly Gly Met Asp Glu Leu Leu Ala Val Leu Gly Tyr Lys<br>50 55 60 | | 192 |
| gtt cgc tcc tca gat atg gcg gat gtg gct ttg aag ttg gag cag ctt<br>Val Arg Ser Ser Asp Met Ala Asp Val Ala Leu Lys Leu Glu Gln Leu<br>65 70 75 80 | | 240 |
| gag atg gtc atg gga act gct tac gaa cat ggg att tct cat ctc gct<br>Glu Met Val Met Gly Thr Ala Tyr Glu His Gly Ile Ser His Leu Ala<br>85 90 95 | | 288 |
| tcc gat act gtt cat tat aat cct tct gat ctc tct tct tgg gtt caa<br>Ser Asp Thr Val His Tyr Asn Pro Ser Asp Leu Ser Ser Trp Val Gln<br>100 105 110 | | 336 |
| aat atg ctc tct gaa ttc aat aat tcc act aac cat ttt aat cct ccc<br>Asn Met Leu Ser Glu Phe Asn Asn Ser Thr Asn His Phe Asn Pro Pro<br>115 120 125 | | 384 |
| cct caa tct tct ccc tat tcc aat tct ccc cac ccc att caa tct acc<br>Pro Gln Ser Ser Pro Tyr Ser Asn Ser Pro His Pro Ile Gln Ser Thr<br>130 135 140 | | 432 |
| aaa tct tgt ttc tac gac gat gat tcg gag tac gat ctt agt gcc att<br>Lys Ser Cys Phe Tyr Asp Asp Asp Ser Glu Tyr Asp Leu Ser Ala Ile<br>145 150 155 160 | | 480 |
| cct ggc gtt gcg gtt tta cct cct aaa gat gaa acc caa act aat tct<br>Pro Gly Val Ala Val Leu Pro Pro Lys Asp Glu Thr Gln Thr Asn Ser<br>165 170 175 | | 528 |
| cgt aag cga ttg aag att gaa aca cag agt agt tcg gtt aat ttg cta<br>Arg Lys Arg Leu Lys Ile Glu Thr Gln Ser Ser Ser Val Asn Leu Leu<br>180 185 190 | | 576 |
| cca tcg ccg tcc tcc tct tcg cca ccg ttc gct tct acg ccg agg att<br>Pro Ser Pro Ser Ser Ser Ser Pro Pro Phe Ala Ser Thr Pro Arg Ile<br>195 200 205 | | 624 |
| gcc tct gaa tct tcg cgg ccg gtg ata gtt gtg gaa gag gat tca caa<br>Ala Ser Glu Ser Ser Arg Pro Val Ile Val Val Glu Glu Asp Ser Gln<br>210 215 220 | | 672 |
| gag act ggg att caa ctt gtt cac gct cta atg gct tgc gct gaa gct<br>Glu Thr Gly Ile Gln Leu Val His Ala Leu Met Ala Cys Ala Glu Ala<br>225 230 235 240 | | 720 |
| gta cag caa gag aat atg aag ctc gcc gat gcg ttg gtg aag cac atc<br>Val Gln Gln Glu Asn Met Lys Leu Ala Asp Ala Leu Val Lys His Ile<br>245 250 255 | | 768 |
| gga ttt ctt gca acg tct caa gcc ggc gct atg agg aaa gtc gcc acg<br>Gly Phe Leu Ala Thr Ser Gln Ala Gly Ala Met Arg Lys Val Ala Thr<br>260 265 270 | | 816 |
| tat ttc gct caa gcc cta gct cgt cgg att tac aga atc tat tct cct<br>Tyr Phe Ala Gln Ala Leu Ala Arg Arg Ile Tyr Arg Ile Tyr Ser Pro<br>275 280 285 | | 864 |
| cag gat gga cta tac tcc tcc tac tcc gat cct ctt cag atg cac ttt<br>Gln Asp Gly Leu Tyr Ser Ser Tyr Ser Asp Pro Leu Gln Met His Phe<br>290 295 300 | | 912 |
| tac gaa acc tgt ccg tat ctg aaa ttc gcg cat ttc act gcc aat caa<br>Tyr Glu Thr Cys Pro Tyr Leu Lys Phe Ala His Phe Thr Ala Asn Gln<br>305 310 315 320 | | 960 |
| gcc att ctt gaa gcg ttc gcg acg gcg gcg aga gtt cat gtc atc gat<br>Ala Ile Leu Glu Ala Phe Ala Thr Ala Ala Arg Val His Val Ile Asp<br>325 330 335 | | 1008 |

```
ttc agt ctt aat caa ggt atg caa tgg ccg gcg ctt atg cag gca ctc    1056
Phe Ser Leu Asn Gln Gly Met Gln Trp Pro Ala Leu Met Gln Ala Leu
            340                 345                 350 gcg ttg cgg cct gga ggt cca ccg gcg ttt cga ttg act gga atc ggc    1104
Ala Leu Arg Pro Gly Gly Pro Pro Ala Phe Arg Leu Thr Gly Ile Gly
        355                 360                 365 ccg ccg cag ccg gta aat ggt ggt tcg ttg cag caa gtc ggt tgg aag    1152
Pro Pro Gln Pro Val Asn Gly Gly Ser Leu Gln Gln Val Gly Trp Lys
    370                 375                 380 tta gcg cag atg gca gag gcc att ggt gtt gat ttc gag ttc aat cac    1200
Leu Ala Gln Met Ala Glu Ala Ile Gly Val Asp Phe Glu Phe Asn His
385                 390                 395                 400 atc gtg tgt agt aat cta gcg gat ctg gat ccg gcg gct ctt gag att    1248
Ile Val Cys Ser Asn Leu Ala Asp Leu Asp Pro Ala Ala Leu Glu Ile
                405                 410                 415 cga ccg tcg gca gtg gag gcg gtg gcg gta aac tcg gtg ttc gat ctg    1296
Arg Pro Ser Ala Val Glu Ala Val Ala Val Asn Ser Val Phe Asp Leu
            420                 425                 430 cac cgg ttg ttg gct cgg cct gga gcg att gag aag gtt ttg gga tcg    1344
His Arg Leu Leu Ala Arg Pro Gly Ala Ile Glu Lys Val Leu Gly Ser
        435                 440                 445 ata aag acg acg aag ccg aag ata gta acg att gtg gaa caa gaa gcg    1392
Ile Lys Thr Thr Lys Pro Lys Ile Val Thr Ile Val Glu Gln Glu Ala
    450                 455                 460 aac cac aac ggt ccg att ttc ctg gac cgg ttt act gag gcg ttg cat    1440
Asn His Asn Gly Pro Ile Phe Leu Asp Arg Phe Thr Glu Ala Leu His
465                 470                 475                 480 tat tac tcg aat ctg ttt gac tcg ttg gaa ggg tct tcg agc ggg ttc    1488
Tyr Tyr Ser Asn Leu Phe Asp Ser Leu Glu Gly Ser Ser Ser Gly Phe
                485                 490                 495 gaa ccg gga agt gag gac gtg ttg ttg tcg gag gtt tat tta gga aag    1536
Glu Pro Gly Ser Glu Asp Val Leu Leu Ser Glu Val Tyr Leu Gly Lys
            500                 505                 510 cag ata tgc aac gtg gtg gct tgt gaa gga acg aac cga gtt gag agg    1584
Gln Ile Cys Asn Val Val Ala Cys Glu Gly Thr Asn Arg Val Glu Arg
        515                 520                 525 cac gaa tca cta agt cag tgg cga agt agg atg gag tcg tcc ggg ttc    1632
His Glu Ser Leu Ser Gln Trp Arg Ser Arg Met Glu Ser Ser Gly Phe
    530                 535                 540 gat ccg gtc cat ctg ggt tca aac gcg ttt aaa caa gct agt atg ctt    1680
Asp Pro Val His Leu Gly Ser Asn Ala Phe Lys Gln Ala Ser Met Leu
545                 550                 555                 560 ttg gcc ctc ttt gca gga gga gaa ggg tac agg gtg gaa gag aat aat    1728
Leu Ala Leu Phe Ala Gly Gly Glu Gly Tyr Arg Val Glu Glu Asn Asn
                565                 570                 575 ggg tgt tta atg ctt ggc tgg cac act aga ccg ttg atc gcg agt cga    1776
Gly Cys Leu Met Leu Gly Trp His Thr Arg Pro Leu Ile Ala Ser Arg
            580                 585                 590 agt gag tgg act ctg tga                                            1794
Ser Glu Trp Thr Leu
        595

<210> SEQ ID NO 4
<211> LENGTH: 597
<212> TYPE: PRT
<213> ORGANISM: Cucumis sativus

<400> SEQUENCE: 4

Met Lys Arg Glu Leu Glu Asp Asp Arg Ser Thr Thr Pro Gly Asp Ala
1               5                   10                  15
```

-continued

```
Pro Arg Ile Val Lys Gly Asp Ser Ser Met Ser Ser Gly Lys Leu
             20                  25                  30

Lys Met Trp Gln Pro His Glu Glu Asp Glu Gly Lys Asp Ala Lys Asp
         35                  40                  45

Gly Ala Ala Gly Gly Met Asp Glu Leu Leu Ala Val Leu Gly Tyr Lys
 50                  55                  60

Val Arg Ser Ser Asp Met Ala Asp Val Ala Leu Lys Leu Glu Gln Leu
 65                  70                  75                  80

Glu Met Val Met Gly Thr Ala Tyr Glu His Gly Ile Ser His Leu Ala
                 85                  90                  95

Ser Asp Thr Val His Tyr Asn Pro Ser Asp Leu Ser Ser Trp Val Gln
             100                 105                 110

Asn Met Leu Ser Glu Phe Asn Asn Ser Thr Asn His Phe Asn Pro Pro
         115                 120                 125

Pro Gln Ser Ser Pro Tyr Ser Asn Ser Pro His Pro Ile Gln Ser Thr
 130                 135                 140

Lys Ser Cys Phe Tyr Asp Asp Asp Ser Glu Tyr Asp Leu Ser Ala Ile
145                 150                 155                 160

Pro Gly Val Ala Val Leu Pro Pro Lys Asp Glu Thr Gln Thr Asn Ser
                 165                 170                 175

Arg Lys Arg Leu Lys Ile Glu Thr Gln Ser Ser Ser Val Asn Leu Leu
             180                 185                 190

Pro Ser Pro Ser Ser Ser Ser Pro Pro Phe Ala Ser Thr Pro Arg Ile
         195                 200                 205

Ala Ser Glu Ser Ser Arg Pro Val Ile Val Val Glu Glu Asp Ser Gln
 210                 215                 220

Glu Thr Gly Ile Gln Leu Val His Ala Leu Met Ala Cys Ala Glu Ala
225                 230                 235                 240

Val Gln Gln Glu Asn Met Lys Leu Ala Asp Ala Leu Val Lys His Ile
                 245                 250                 255

Gly Phe Leu Ala Thr Ser Gln Ala Gly Ala Met Arg Lys Val Ala Thr
             260                 265                 270

Tyr Phe Ala Gln Ala Leu Ala Arg Arg Ile Tyr Arg Ile Tyr Ser Pro
         275                 280                 285

Gln Asp Gly Leu Tyr Ser Ser Tyr Ser Asp Pro Leu Gln Met His Phe
 290                 295                 300

Tyr Glu Thr Cys Pro Tyr Leu Lys Phe Ala His Phe Thr Ala Asn Gln
305                 310                 315                 320

Ala Ile Leu Glu Ala Phe Ala Thr Ala Ala Arg Val His Val Ile Asp
                 325                 330                 335

Phe Ser Leu Asn Gln Gly Met Gln Trp Pro Ala Leu Met Gln Ala Leu
             340                 345                 350

Ala Leu Arg Pro Gly Gly Pro Pro Ala Phe Arg Leu Thr Gly Ile Gly
         355                 360                 365

Pro Pro Gln Pro Val Asn Gly Gly Ser Leu Gln Gln Val Gly Trp Lys
 370                 375                 380

Leu Ala Gln Met Ala Glu Ala Ile Gly Val Asp Phe Glu Phe Asn His
385                 390                 395                 400

Ile Val Cys Ser Asn Leu Ala Asp Leu Asp Pro Ala Ala Leu Glu Ile
                 405                 410                 415

Arg Pro Ser Ala Val Glu Ala Val Ala Val Asn Ser Val Phe Asp Leu
             420                 425                 430
```

```
His Arg Leu Leu Ala Arg Pro Gly Ala Ile Glu Lys Val Leu Gly Ser
            435                 440                 445

Ile Lys Thr Thr Lys Pro Lys Ile Val Thr Ile Val Glu Gln Glu Ala
    450                 455                 460

Asn His Asn Gly Pro Ile Phe Leu Asp Arg Phe Thr Glu Ala Leu His
465                 470                 475                 480

Tyr Tyr Ser Asn Leu Phe Asp Ser Leu Glu Gly Ser Ser Ser Gly Phe
                485                 490                 495

Glu Pro Gly Ser Glu Asp Val Leu Leu Ser Glu Val Tyr Leu Gly Lys
            500                 505                 510

Gln Ile Cys Asn Val Val Ala Cys Glu Gly Thr Asn Arg Val Glu Arg
        515                 520                 525

His Glu Ser Leu Ser Gln Trp Arg Ser Arg Met Glu Ser Ser Gly Phe
    530                 535                 540

Asp Pro Val His Leu Gly Ser Asn Ala Phe Lys Gln Ala Ser Met Leu
545                 550                 555                 560

Leu Ala Leu Phe Ala Gly Gly Glu Gly Tyr Arg Val Glu Glu Asn Asn
                565                 570                 575

Gly Cys Leu Met Leu Gly Trp His Thr Arg Pro Leu Ile Ala Ser Arg
            580                 585                 590

Ser Glu Trp Thr Leu
        595

<210> SEQ ID NO 5
<211> LENGTH: 1761
<212> TYPE: DNA
<213> ORGANISM: Cucumis sativus
<220> FEATURE:
<221> NAME/KEY: CDS
<222> LOCATION: (1)..(1758)

<400> SEQUENCE: 5 atg aag agg gag cat cac cat ctt cat cca cgt ccg gag ccg cct tcc    48
Met Lys Arg Glu His His His Leu His Pro Arg Pro Glu Pro Pro Ser
1               5                   10                  15 atg gct gtc gtc cct aat ggg gag agt ttt ttg aat acc ggt aag gct    96
Met Ala Val Val Pro Asn Gly Glu Ser Phe Leu Asn Thr Gly Lys Ala
            20                  25                  30 aag ctc tgg gaa gag gaa gcc cag ctc gat gga gga atg gat gag ctt   144
Lys Leu Trp Glu Glu Glu Ala Gln Leu Asp Gly Gly Met Asp Glu Leu
        35                  40                  45 ctt gct gtt ttg ggt tat aag gtt aag tcc tcg gac atg gcg gat gtt   192
Leu Ala Val Leu Gly Tyr Lys Val Lys Ser Ser Asp Met Ala Asp Val
    50                  55                  60 gct cag aag ctt gaa caa ctt gaa gaa gct atg tgt caa gtt cag gat   240
Ala Gln Lys Leu Glu Gln Leu Glu Glu Ala Met Cys Gln Val Gln Asp
65                  70                  75                  80 act ggt ctt tct cat ctt gct ttt gat act gtt cat tat aat cct tct   288
Thr Gly Leu Ser His Leu Ala Phe Asp Thr Val His Tyr Asn Pro Ser
                85                  90                  95 gat ctg tct act tgg ctt gaa agt atg ctc acc gag ctc cat ccg atg   336
Asp Leu Ser Thr Trp Leu Glu Ser Met Leu Thr Glu Leu His Pro Met
            100                 105                 110 cct aat ttt gcg acg ccg cca cct cct tcg cag ctg gac gat cct tcg   384
Pro Asn Phe Ala Thr Pro Pro Pro Pro Ser Gln Leu Asp Asp Pro Ser
        115                 120                 125 ttt tta gct ccg gcg gaa tcc tcc acc atc act tcc att gat tat gac   432
Phe Leu Ala Pro Ala Glu Ser Ser Thr Ile Thr Ser Ile Asp Tyr Asp
    130                 135                 140
```

-continued

| | |
|---|---|
| cct cag cgg caa act agc agc cgg att ttc gag gaa tct tct agt tct<br>Pro Gln Arg Gln Thr Ser Ser Arg Ile Phe Glu Glu Ser Ser Ser Ser<br>145                    150                 155                  160 | 480 |
| gat tac gac ctt aaa gct atc acg agc agt gcg att tat tca ccg aga<br>Asp Tyr Asp Leu Lys Ala Ile Thr Ser Ser Ala Ile Tyr Ser Pro Arg<br>                 165                  170                 175 | 528 |
| gag aat aaa cgt ttg aaa tct tcc gag tcg gac tca gat gtg ttc tct<br>Glu Asn Lys Arg Leu Lys Ser Ser Glu Ser Asp Ser Asp Val Phe Ser<br>            180                  185                 190 | 576 |
| acc tcg gcg att agg gct tcc gat tct gta act cgt cct gtc gtc ctc<br>Thr Ser Ala Ile Arg Ala Ser Asp Ser Val Thr Arg Pro Val Val Leu<br>     195                  200                 205 | 624 |
| gtc gat tcg cag gag aac gga att caa ctg gtc cat gcg ttg atg gct<br>Val Asp Ser Gln Glu Asn Gly Ile Gln Leu Val His Ala Leu Met Ala<br>210                    215                 220 | 672 |
| tgc gcc gaa gcc gta cag cag aac aat ctg aat ata gcg gag gct ctg<br>Cys Ala Glu Ala Val Gln Gln Asn Asn Leu Asn Ile Ala Glu Ala Leu<br>225                    230                 235                 240 | 720 |
| gtg aag cga atc ggt tac ttg gcg gtt tct caa gca gga gcg atg agg<br>Val Lys Arg Ile Gly Tyr Leu Ala Val Ser Gln Ala Gly Ala Met Arg<br>                 245                 250                 255 | 768 |
| aag gtc gcc acg ttc ttc gct gaa gcg ttg gct cgc cga atc tac agg<br>Lys Val Ala Thr Phe Phe Ala Glu Ala Leu Ala Arg Arg Ile Tyr Arg<br>            260                  265                 270 | 816 |
| ctc tgc cct gag aat ccc ctc gat cat tca gtg tcc gat agg ctt cag<br>Leu Cys Pro Glu Asn Pro Leu Asp His Ser Val Ser Asp Arg Leu Gln<br>     275                  280                 285 | 864 |
| atg cat ttc tac gag agc tgt ccc tat ctg aaa ttc gcg cat ttc acc<br>Met His Phe Tyr Glu Ser Cys Pro Tyr Leu Lys Phe Ala His Phe Thr<br>290                    295                 300 | 912 |
| gcg aat caa gcg att ctc gaa gct ttc gaa ggg aag aaa cgt gtt cac<br>Ala Asn Gln Ala Ile Leu Glu Ala Phe Glu Gly Lys Lys Arg Val His<br>305                    310                 315                 320 | 960 |
| gta atc gat ttc tcg atg aac cga ggg atg caa tgg cca gct ctg att<br>Val Ile Asp Phe Ser Met Asn Arg Gly Met Gln Trp Pro Ala Leu Ile<br>                 325                  330                 335 | 1008 |
| caa gcc cta gct cta cgg ccg aac ggt cct cca gcc ttc cgc ctc acc<br>Gln Ala Leu Ala Leu Arg Pro Asn Gly Pro Pro Ala Phe Arg Leu Thr<br>            340                  345                 350 | 1056 |
| ggg att ggt cct ccg gcg ccg gat aac tca gat tac ctc caa gaa gta<br>Gly Ile Gly Pro Pro Ala Pro Asp Asn Ser Asp Tyr Leu Gln Glu Val<br>     355                  360                 365 | 1104 |
| ggc tgg aaa ctg gct gaa tta gcc gaa gct atc cat gtg gac ttc gaa<br>Gly Trp Lys Leu Ala Glu Leu Ala Glu Ala Ile His Val Asp Phe Glu<br>370                    375                 380 | 1152 |
| tac aga gga ttt gtg gcg aat agt tta gca gat cta gac gcg tcg atg<br>Tyr Arg Gly Phe Val Ala Asn Ser Leu Ala Asp Leu Asp Ala Ser Met<br>385                    390                 395                 400 | 1200 |
| ctg gag ctc cga ccg agc gag gtt gaa tcg gtg gtg gtg aac tca gta<br>Leu Glu Leu Arg Pro Ser Glu Val Glu Ser Val Val Val Asn Ser Val<br>            405                  410                 415 | 1248 |
| ttc gag tta cat aag ctc ctg gct cgg cct ggt gcc ctg gaa aag gtt<br>Phe Glu Leu His Lys Leu Leu Ala Arg Pro Gly Ala Leu Glu Lys Val<br>                 420                  425                 430 | 1296 |
| ctg tcg gtg gtg aaa cag atg aag ccg gag atc atg acg gtg gtg gag<br>Leu Ser Val Val Lys Gln Met Lys Pro Glu Ile Met Thr Val Val Glu<br>            435                  440                 445 | 1344 |
| caa gaa gcg aat cac aac ggt ccg gta ttc gtg gac cgg ttc act gag<br>Gln Glu Ala Asn His Asn Gly Pro Val Phe Val Asp Arg Phe Thr Glu | 1392 |

```
                450             455             460
tca ctc cat tac tac tca acg ctt ttt gac tcg ttg gaa ggc tcc ccc        1440
Ser Leu His Tyr Tyr Ser Thr Leu Phe Asp Ser Leu Glu Gly Ser Pro
465                 470                 475                 480 aac aac cag gat aaa atc atg tcc gaa atg tac ctt gga aag caa att        1488
Asn Asn Gln Asp Lys Ile Met Ser Glu Met Tyr Leu Gly Lys Gln Ile
                485                 490                 495 tgc aac gtc gtg gct tgt gaa ggt gcc gac cgt gtc gaa cgc cac gag        1536
Cys Asn Val Val Ala Cys Glu Gly Ala Asp Arg Val Glu Arg His Glu
        500                 505                 510 acc tta act cag tgg caa act cgg tta tcc tcc gcc ggg ttc gaa ccc        1584
Thr Leu Thr Gln Trp Gln Thr Arg Leu Ser Ser Ala Gly Phe Glu Pro
            515                 520                 525 atc cac ctc ggc tca aac gca ttc aaa caa gca agc atg ctc ctc gcc        1632
Ile His Leu Gly Ser Asn Ala Phe Lys Gln Ala Ser Met Leu Leu Ala
                530                 535                 540 cta ttc ggc agt gga gag ggg tac cgg gtg gaa gag aac aac gga tca        1680
Leu Phe Gly Ser Gly Glu Gly Tyr Arg Val Glu Glu Asn Asn Gly Ser
545                 550                 555                 560 cta atg cta gga tgg cac act cgc cca ctc ata gcc acc tcc gct tgg        1728
Leu Met Leu Gly Trp His Thr Arg Pro Leu Ile Ala Thr Ser Ala Trp
                565                 570                 575 aaa atc ggc aac aac ccg gtg gtc gct aag tga                            1761
Lys Ile Gly Asn Asn Pro Val Val Ala Lys
                580                 585
```

<210> SEQ ID NO 6
<211> LENGTH: 586
<212> TYPE: PRT
<213> ORGANISM: Cucumis sativus

<400> SEQUENCE: 6

```
Met Lys Arg Glu His His His Leu His Pro Arg Pro Glu Pro Pro Ser
1               5                   10                  15

Met Ala Val Val Pro Asn Gly Glu Ser Phe Leu Asn Thr Gly Lys Ala
            20                  25                  30

Lys Leu Trp Glu Glu Glu Ala Gln Leu Asp Gly Gly Met Asp Glu Leu
        35                  40                  45

Leu Ala Val Leu Gly Tyr Lys Val Lys Ser Ser Asp Met Ala Asp Val
    50                  55                  60

Ala Gln Lys Leu Glu Gln Leu Glu Glu Ala Met Cys Gln Val Gln Asp
65                  70                  75                  80

Thr Gly Leu Ser His Leu Ala Phe Asp Thr Val His Tyr Asn Pro Ser
                85                  90                  95

Asp Leu Ser Thr Trp Leu Glu Ser Met Leu Thr Glu Leu His Pro Met
            100                 105                 110

Pro Asn Phe Ala Thr Pro Pro Pro Ser Gln Leu Asp Asp Pro Ser
        115                 120                 125

Phe Leu Ala Pro Ala Glu Ser Ser Thr Ile Thr Ser Ile Asp Tyr Asp
    130                 135                 140

Pro Gln Arg Gln Thr Ser Ser Arg Ile Phe Glu Glu Ser Ser Ser
145                 150                 155                 160

Asp Tyr Asp Leu Lys Ala Ile Thr Ser Ala Ile Tyr Ser Pro Arg
                165                 170                 175

Glu Asn Lys Arg Leu Lys Ser Ser Glu Ser Asp Ser Asp Val Phe Ser
            180                 185                 190

Thr Ser Ala Ile Arg Ala Ser Asp Ser Val Thr Arg Pro Val Val Leu
```

```
                195                 200                 205
    Val Asp Ser Gln Glu Asn Gly Ile Gln Leu Val His Ala Leu Met Ala
    210                 215                 220

Cys Ala Glu Ala Val Gln Asn Asn Leu Asn Ile Ala Glu Ala Leu
225                 230                 235                 240

Val Lys Arg Ile Gly Tyr Leu Ala Val Ser Gln Ala Gly Ala Met Arg
                    245                 250                 255

Lys Val Ala Thr Phe Phe Ala Glu Ala Leu Ala Arg Arg Ile Tyr Arg
                    260                 265                 270

Leu Cys Pro Glu Asn Pro Leu Asp His Ser Val Ser Asp Arg Leu Gln
                    275                 280                 285

Met His Phe Tyr Glu Ser Cys Pro Tyr Leu Lys Phe Ala His Phe Thr
                    290                 295                 300

Ala Asn Gln Ala Ile Leu Glu Ala Phe Glu Gly Lys Lys Arg Val His
    305                 310                 315                 320

Val Ile Asp Phe Ser Met Asn Arg Gly Met Gln Trp Pro Ala Leu Ile
                    325                 330                 335

Gln Ala Leu Ala Leu Arg Pro Asn Gly Pro Pro Ala Phe Arg Leu Thr
                    340                 345                 350

Gly Ile Gly Pro Pro Ala Pro Asp Asn Ser Asp Tyr Leu Gln Glu Val
                    355                 360                 365

Gly Trp Lys Leu Ala Glu Leu Ala Glu Ala Ile His Val Asp Phe Glu
                    370                 375                 380

Tyr Arg Gly Phe Val Ala Asn Ser Leu Ala Asp Leu Asp Ala Ser Met
    385                 390                 395                 400

Leu Glu Leu Arg Pro Ser Glu Val Glu Ser Val Val Asn Ser Val
                    405                 410                 415

Phe Glu Leu His Lys Leu Leu Ala Arg Pro Gly Ala Leu Glu Lys Val
                    420                 425                 430

Leu Ser Val Val Lys Gln Met Lys Pro Glu Ile Met Thr Val Val Glu
                    435                 440                 445

Gln Glu Ala Asn His Asn Gly Pro Val Phe Val Asp Arg Phe Thr Glu
                    450                 455                 460

Ser Leu His Tyr Tyr Ser Thr Leu Phe Asp Ser Leu Glu Gly Ser Pro
    465                 470                 475                 480

Asn Asn Gln Asp Lys Ile Met Ser Glu Met Tyr Leu Gly Lys Gln Ile
                    485                 490                 495

Cys Asn Val Val Ala Cys Glu Gly Ala Asp Arg Val Glu Arg His Glu
                    500                 505                 510

Thr Leu Thr Gln Trp Gln Thr Arg Leu Ser Ser Ala Gly Phe Glu Pro
                    515                 520                 525

Ile His Leu Gly Ser Asn Ala Phe Lys Gln Ala Ser Met Leu Leu Ala
                    530                 535                 540

Leu Phe Gly Ser Gly Glu Gly Tyr Arg Val Glu Glu Asn Asn Gly Ser
    545                 550                 555                 560

Leu Met Leu Gly Trp His Thr Arg Pro Leu Ile Ala Thr Ser Ala Trp
                    565                 570                 575

Lys Ile Gly Asn Asn Pro Val Val Ala Lys
                    580                 585
```